US007871608B2

(12) United States Patent
Zimmerman et al.

(10) Patent No.: US 7,871,608 B2
(45) Date of Patent: *Jan. 18, 2011

(54) REVERSIBLY INACTIVATED ACIDIFIED PLASMIN

(75) Inventors: Thomas P. Zimmerman, Raleigh, NC (US); Valery Novokhatny, Raleigh, NC (US); Shan Jiang, Cary, NC (US); James Colandene, Raleigh, NC (US)

(73) Assignee: Talecris Biotherapeutics, Inc., Research Triangle Park, NC (US)

( * ) Notice: Subject to any disclaimer, the term of this patent is extended or adjusted under 35 U.S.C. 154(b) by 28 days.

This patent is subject to a terminal disclaimer.

(21) Appl. No.: 12/197,617

(22) Filed: Aug. 25, 2008

(65) Prior Publication Data

US 2008/0311105 A1 Dec. 18, 2008

Related U.S. Application Data

(60) Division of application No. 10/143,112, filed on May 10, 2002, which is a continuation of application No. PCT/US00/31090, filed on Nov. 13, 2000, which is a continuation-in-part of application No. 09/438,331, filed on Nov. 13, 1999, now Pat. No. 6,355,243.

(51) Int. Cl.
C12N 9/48 (2006.01)
C12N 9/72 (2006.01)
C13N 9/68 (2006.01)
(52) U.S. Cl. ................. 424/94.64; 424/94.63; 435/212; 435/215; 435/217
(58) Field of Classification Search .................. None
See application file for complete search history.

(56) References Cited

U.S. PATENT DOCUMENTS

| | | |
|---|---|---|
| 3,136,703 A | 6/1964 | Singher |
| 3,434,929 A | 3/1969 | Buck et al. |
| 3,865,692 A | 2/1975 | Holleman et al. |
| 3,950,223 A | 4/1976 | Yugari et al. |
| 3,950,513 A | 4/1976 | Jensen |
| 4,082,612 A | 4/1978 | Robbins et al. |
| 4,115,551 A | 9/1978 | Lormeau et al. |
| 4,177,262 A | 12/1979 | Lormeau et al. |
| 4,259,448 A | 3/1981 | Nakamura et al. |
| 4,361,652 A | 11/1982 | Uemura et al. |
| 4,361,653 A | 11/1982 | Watanabe et al. |
| 4,418,052 A | 11/1983 | Wong |
| 4,442,213 A | 4/1984 | Heber et al. |
| 4,446,316 A | 5/1984 | Chazov et al. |
| 4,462,980 A | 7/1984 | Diedrichsen et al. |
| 4,499,073 A | 2/1985 | Tenold |
| 4,663,146 A | 5/1987 | Morser et al. |
| 4,774,087 A | 9/1988 | Wu et al. |
| 4,908,204 A | 3/1990 | Robinson et al. |
| 5,024,829 A | 6/1991 | Berger et al. |
| 5,068,106 A | 11/1991 | Paques et al. |
| 5,096,637 A | 3/1992 | DiLeo et al. |
| 5,112,609 A | 5/1992 | Johnston et al. |
| 5,165,912 A | 11/1992 | Selmer et al. |
| 5,237,050 A | 8/1993 | Boyle et al. |
| 5,288,489 A | 2/1994 | Reich et al. |
| 5,290,692 A | 3/1994 | Suzuki et al. |
| 5,304,383 A | 4/1994 | Eibl et al. |
| 5,328,996 A | 7/1994 | Boyle |
| 5,371,007 A | 12/1994 | Linnau et al. |
| 5,407,673 A | 4/1995 | Reich et al. |
| 5,407,678 A | 4/1995 | Rose et al. |
| 5,472,692 A | 12/1995 | Liu et al. |
| 5,587,291 A | 12/1996 | Binder |
| 5,728,674 A | 3/1998 | Sprecher et al. |
| 5,767,269 A | 6/1998 | Hirsh et al. |
| 5,776,452 A | 7/1998 | Eibl et al. |
| 5,879,923 A | 3/1999 | Yago et al. |
| 5,928,218 A | 7/1999 | Gelbfish |
| 6,139,819 A | 10/2000 | Unger et al. |
| 6,207,066 B1 | 3/2001 | Trese et al. |
| 6,355,243 B1 | 3/2002 | Novokhatny et al. |
| 6,479,253 B1 | 11/2002 | Silver et al. |
| 6,694,764 B1 | 2/2004 | Eckstein, Jr. et al. |
| 6,969,515 B2 | 11/2005 | Jesmok et al. |

FOREIGN PATENT DOCUMENTS

CN 1 167 823 A 12/1997

(Continued)

OTHER PUBLICATIONS

Abe, et al., "Immobilized urokinase column as part of a specific detection system for plasminogen species separated by high-performance affinity chromatography," J. Chromatography, 1991, vol. 565, pp. 183-195.
Ambrus, et al., "Clinical and experimental studies on fibrinolytic enzymes," Ann NY Acad Sci., Aug. 30, 1957, vol. 68, No. 1, pp. 97-137.
Amris, et al., "Clinical studies on an activator free porcine plasma (plasmin-novo)," Sangre (Barc), 1964, vol. 61, pp. 12-18.
Deacon, et al., "Technetium 99m-plasmin: a new test for the detection of deep vein thrombosis," Eur J. Nucl. Med., 1980, vol. 53, No. 631, pp. 673-677.
Gottfried Schmer, "The purification of bovine thrombin by affinity chromatography on benzamidine-agarose," Hoppe Seyler's Z Physiol Chem., May 1972, vol. 353, pp. 810-814.
Greig, et al., "Protamine-Heparin complex as a substrate for plasmin," Biochim. Biophys. Acia., 1963, vol. 67, pp. 658-668.

(Continued)

Primary Examiner—Michele Flood
(74) Attorney, Agent, or Firm—Womble Carlyle Sandridge & Rice PLLC

(57) ABSTRACT

A method of treating a subject, the method including administring a composition that includes a reversibly inactivated acidfied plasmin substantially free of a plasminogen activator, in a low buffering capacity buffer, wherein the composition is a solution suitable for pharmacenutical use that can be raised to physiological pH by adding no more than about 5 volumes of serum to the solution relative to a volume of the solution.

20 Claims, 10 Drawing Sheets

FOREIGN PATENT DOCUMENTS

| | | |
|---|---|---|
| DE | 3617753 A1 | 12/1986 |
| EP | 0256836 A1 | 8/1987 |
| EP | 0256836 A1 | 2/1988 |
| EP | 0297294 A1 | 1/1989 |
| EP | 0 399 321 A2 | 11/1990 |
| GB | 904478 | 8/1962 |
| GB | 985498 A | 3/1965 |
| GB | 2 090 599 A | 7/1982 |
| JP | 0207 8633 | 3/1990 |
| JP | 09 065895 A | 3/1997 |
| RO | 103 682 A | 12/1991 |
| WO | WO 87/06836 A | 11/1987 |
| WO | WO 93/15189 A | 8/1993 |
| WO | WO 95 04077 A1 | 2/1995 |
| WO | WO 97/15572 | 5/1997 |
| WO | WO 98/37086 | 8/1998 |

OTHER PUBLICATIONS

In "Pharmaceutical Enzymes" (eds. R. Ruyssen & A. Lauwers)-Story Scientia, Gent, Belgium, 1978, pp. 124-131.

Owunwanne, et al., "Technetium Tc 99m plasmin in the diagnosis of inflammatory disease," Eur J. Nucl. Med., 1987, vol. 12, No. 10, pp. 496-499.

Shi, et al., "Differential autolysis of human plasmin at various pH levels," Thrombosis Research, 1988, vol. 51, pp. 355-364.

Shimura, et al., "High-performace affinity chromatography of plasmin and plasminogen on a hydrophilic vinyl-polymer gel coupled with p-aminobenzamidine," J. Chromatography, 1984, vol. 292, pp. 369-382.

S. Shaukat Husain, "A single-step separation of the one-and two-chain forms of tissue plasminogen activator[1]," Arch Biochem Biophys., 1991, vol. 285, pp. 373-376.

Alkjaersig, N., et al., "The Activation of Human Plasminogen," J. Biol. Chem., 233(1): 81-85 (1958).

Alkjaersig, N., et al., "The Mechanism of Clot Dissolution by Plasmin," J. Clin. Invest., 38(7): 1086-1095 (1959).

Ambrus, C., et al., "Insolubilized Activators of the Fibrinolysin System," J. Med. 3:270-281 (1972).

Ambrus, J.L., et al., "Clinical Pharmacology of various types of fibrinolytic enzyme preparations," Am. J. Cardiol., 6:462-475 (1960).

Amris, C.J., et al., "Effect of Plasmin Therapy on Blood Coagulation and on Plasma Proteins in Patients with Cancer," Danish Medical Bulletin, 11(5):141-145 (1964).

Amris, C.J., et al., "Turnover and Distribution of [131]I-Labelled Procine Plasmin in Man and Dog," Danish Medical Bulletin, 11(5):146-152 (1964).

Anlyan, W., et al., "Experiences with Fibrinolysin in Peripheral Vascular Occlusive Disease," Am. J. Cardiol., 6:507-512 (1960).

Barrett, A.J., et al., "The Electrophoretically 'Slow' and 'Fast' Forms of the α2-Macroglobulin Molecule," Biochem. J., 181:401-418 (1979).

Becker, Gary J., "Local Thrombolytic Therapy: Bridging the 'Generation Gap,'" Am. J. Roentgenol., 140(2): 403-405 (1983).

Binder, B.R., et al., "Purification and Characterization of Human Vascular Plasminogen Activator Derived from Blood Vessel Perfusates," Journal of Biological Chemistry, 254(6):1998-2003 (1979).

Boucek, R., et al., "Segmental Perfusion of the Coronary Arteries with Fibrinolysin in Man Following a Myocardial Infarction," Am. J. Cardiol., 6:525-533 (1960).

Boyles, P.W., et al., "Comparative effectiveness of intravenous and intra-arterial fibrinolysin therapy," Am. J. Cardiol., 6:439-446 (1960).

Castellino, F.J. and J.R. Powell, "Human Plasminogen," Meth. Enzymology, 80:365-378 (1981).

Castellino, F.J., et al., "Rabbit Plasminogen and Plasmin Isozymes," Methods in Enzymology, 45:273-286 (1976).

Collen D., et al., "Thrombolysis with human extrinsic (tissue-type) plasminogen activator in rabbits with experimental jugular vein thrombosis. Effect of molecular form and dose of activator, age of the thrombus, and route of administration," J. of Clin. Invest., 71(2):368-376 (1983).

Deutsch, D.G. and E.T. Mertz, "Plasminogen: purification from human plasma by affinity chromatography," Science 170:1095-1096 (1970).

Freitag, H., et al., "Lys-plasminogen as an Adjunct to Local Intra-arterial Fibrinolysis of Carotid Territory Stroke: Laboratory and Clinical Findings," Neuroradiology, 38:181-185 (1996).

Hedner, U., et al., "Effects of Porcine Plasmin on the Coagulation and Fibrinolytic Systems in Humans," Blood, 51(1):157-164 (1978).

Holmberg, L., et al., "Purification of Urokinase by Affinity Chromatography," Biochim. Biophys. Acta., 445: 215-222 (1976).

Jespersen, J., et al., "The autodigestion of human plasmin follows a bimolecular mode of reaction subject to product inhibition," Thromb. Res. 41(3):395-404 (1986).

Johnson, A.J., et al., "Assay methods and standard preparations for plasmin, plasminogen and urokinase in purified systems, 1967-1968," Thromb. Diath. Haemorrh., 21(2):259-72 (1969).

Kirkwood, T.B.L., et al., "A standard for human plasmin," Thromb. Diath. Haemorrh., 34(1):20-30 (1975).

Kitamoto, Y., et al., "A Femoral Vein Catheter with Immobilized Urokinase (UKFC) as an Antithrombotic Blood Access," Trans. Am. Soc. Artif. Intern. Organs, 33:136-139 (1987).

Kline, D.L., "The Purification and Crystallization of Plasminogen (Profibrinolysin)," Journal of Biological Chemistry, 204:949-955 (1953).

Kline, D.L. and J.B. Fishman, Preparation, Stabilization and Some Properties of Purified Human Plasmin, Thromb. Diath. Haemorrh., 11:75-84 (1964).

Larsen, V., "Fibrinolytic Enzyme in the Treatment of Patients with Cancer," Danish Medical Bulletin, 2(5):137-140 (1964).

Larson, V., et al., "Fibrinolytic Treatment with Activator-Free Porcine Plasmin," Scand. J. Clin. Invest. 18(Suppl. 89):34-73 (1966).

Lijnen, H.R., et al., "Activation of plasminogen by pro-urokinase," J. Biol. Chem., 261(1):1253-1258 (1986).

Ling, C.M., et al., "Mechanism of formation of bovine plasminogen activator from human plasmin," J. Biol. Chem., 240(11):4213-8 (1965).

Lippschutz, E.L., et al., "Controlled study of the treatment of coronary occulsion with urokinase-activated human plasmin," Am. J. Cardiol., 16:93-98 (1965).

Mathey D.G., et al., "Intravenous Urokinase in Acute Myocardial Infarction," Am. J. Cardiol., 55:878-882 (1985).

Mizutani et al. "Potential thrombolysis under selective infusion of autolotous plasmin (AP) solution," Japanese Heart Journal, 30(5):723-732 (1989).

Moser, K., "Effects of Intravenous Administration of Fibrinolysin (Plasmin) in Man," Circulation, 20:42-55 (1959).

Nahum, L.H., et al., "Fibrinolysis. II. Evaluation of enzymatic thrombolysis: Experiments with plasmin preparations in arterial, venous thrombosis," Conn. Med. 24:139-46 (1960).

Nilsson, T. and B. Wiman, "On the structure of the stable complex between plasmin and alpha-2-antiplasmin," FEBS Lett., 142(1):111-114 (1982).

Novokhatny, V. et al. "Thrombolytic potential of locally delivered active plasmin (Pm): In vitro assessment and in vivo comparison with tPA in the rabbit jugular vein trombosis model," Blood, 92(10) Suppl. 2, Abstract 3400. (Nov. 15, 1998).

Novokhatny, V., et al., "Thrombolytic potency of acid-stabilized plasmin: superiority over tissue-type plasminogen activator in an in vitro model of catheter-assisted thrombolysis," J. Thromb. Haemost., 1:1034-1041 (2003).

Petitpretz, P., et al., "Effects of a single bolus of urokinase in patients with life-threatening pulmonary emboli: a descriptive trial," Circulation, 70(5): 861-866 (1984).

Robbins, K.C. and L. Summaria, "Plasminogen and Plasmin," Meth. Enzymol. 45:257-273 (1976).

Robbins, K.C. et al. "Purification of Human Plasminogen and Plasmin by Gel Filtration of Sephadex and Chromatography on Diethylaminoethyl Sephadex". Journal of Biological Chemistry (1963), vol. 238, pp. 952-962.

Robbins, K.C., et al., "Human Plasminogen and Plasmin," *Methods in Enzymology*, 19:184-199 (1970).

Robbins, K.C., et al., "The peptide chains of human plasmin. Mechanism of activation of human plasminogen to plasmin," *J. Biol. Chem.*, 242(10):2333-42 (1967).

Seifert, V., et al., "Efficacy of Single Intracisternal Bolus Injection of Recombinant Tissue Plasminogen Activator to Prevent Delayed Cerebral Vasospasm after Experimental Subarachnoid Hemorrhage," *Neurosurgery*, 25(4): 590-598 (1989).

Sgouris, J,T, et al. "The preparation of human fibrinolysin (plasmin)," *Vox Sang.*, 5:357-76 (1960).

Sherry S., "The Origin of Thrombolytic Therapy," *J. Am. Coll. Cardiol.*, 14(4):1085-1092 (1989).

Summaria, L., et al., "Recombinant human Lys-plasmin and the Lys-plasmin streptokinase complex," *J. Biol. Chem.*, 254(14):6811-4 (1979).

Summaria, L., et al., "The specific mechanism of activation of human plasminogen to plasmin," *J. Biol. Chem.*, 242(19):4279-83 (1967).

Ueshima, S., et al., "Stabilization of plasmin by lysine derivatives," *Clin. Chim. Acta.*, 245(1):7-18 (1996).

Verstraete, M., "The Fibrinolytic System: from Petri Dishes to Genetic Engineering," *Thrombosis and Haemostasis*, 74(1):25-35 (1995).

Wiman, B., "Affinity-chromatographic purification of human alpha 2-antiplasmin," *Biochem. J.*, 191(1):229-232 (1980).

Wiman, B., and Per Wallén, "Activation of Human Plasminogen by an Insoluble Derivative of Urokinase Structural Changes of Plasminogen in the course of Activation to Plasmin and Demonstration of a Possible Intermediate Compound," *Eur. J. Biochem.*, 36(1): 25-31 (1973).

Wohl, R.C., et al., "Kinetics of activation of human plasminogen by different activator species at pH 7.4 and 37° C.," *J. Biol. Chem.*, 255(5):2005-13 (1980).

Wohl, R.C., et al., "Steady state kinetics of activation of human and bovine plasminogens by streptokinase and its equimolar complexes with various activated forms of human plasminogen," *J. Biol. Chem.*, 253(5):1402-7 (1978).

http://www.lakesidepress.com/pulmonary/books/physiology/chap7_1.htm, Chapter 7: Acid-Base Balance.

European Supplementary Partial Search Report (EP 00 97 8572, dated Jul. 16, 2004).

European Supplementary Partial Search Report (EP 00 99 0910, dated May 25, 2004).

European Supplementary Partial Search Report (EP 00 99 1956, dated Jun. 1, 2004).

International Search Report (PCT/US03/34020, dated Jul. 27, 2004).

Supplementary Partial European Search Report (EP 00 99 1956, dated Dec. 17, 2004).

Extended European Search Report (EP 1 956 082 A1, dated Jul. 10, 2008).

Abe, T., "Fibrinolytic Influence of monocarbonic acids and some other substances," Proc. Intern. Cong. Hematol., (1962), vol. 3; pp. 1587-39.

Amor, M., et al., "Thrombectomy with the hydrolysing catheter," Archives des Maladies du Couer et des Vaisseaux, (1997), vol. 90, No. 6, pp. 797-804.

Amris, C.J., et al., "Infusion of porcine plasmin in man," Scandivav. J. Clin. & Lab. Investigation, (1963), vol. 15, pp. 179-188.

Barth, K.H. et al., "Multicenter prospective randomized comparison between a mechanical thrombectomy systems (OASIS) and pulespray thrombolysis for thrombosed hemodialysis grafts," Radiology, (Nov. 1998) vol. 209P, Supp. [S]: 714.

Beathard, G. A., "Mechanical versus pharmacomechanical thrombolysis for the treatment of thrombosed dialysis access grafts," Kidney International, (1994), vol. 45, pp. 1401-1406.

Bookstein, J.J., et al., How I Do It: "Pulse-spray pharmacomechanical thrombolysis," Cardiovasc. Intervent Radiol., (1992) vol. 15, pp. 228-233.

Decision of the Board of Patent Appeals and Interferences dated Feb. 19, 2008 in Appeal No. 2007-0545, Ex parte Thomas P. Zimmerman, Valery Novokhatny, Shang Jiang and James Colancleve (with claims considered on Appeal).

Dupe, RJ et al., "Acyl-enzymes as thrombolytic agents in dog models of venous thrombosis and pulmonary embolism," Thrombosis and Haemostasis, (1981), vol. 51, No. 2, pp. 248-253.

Freitag et al., "Lys-plasminogen as an adjunct to local intra-arterial fibrinolysis for carotid territory stroke: laboratory and clinical findings," Neuroradiology 38: 181-185 (1996).

Lazzaro, C.R. et al., "Modified use of the arrow-trerotola percutaneous thrombolytic device for the treatment of trombosed hemodialysis access grafts[1]," J. Vasc Inter Radiol, (Sep. 1999), vol. 10, No. 8, pp. 1025-1031.

Martin, et al., "Pulmonary Physiology in Clinical Practice, The Essentials for Patient Care and Evaluation," The C.V. Mosby Company, 1987, Chapt. 7, Acid-base balance, pp. 129-146.

Ouellette, "Introduction to General, Organic, and Biological Chemistry," Second Edition (1988). The Ohio State University. Macmillan Publishing Company, New York, NY, pp. 288-290.

Schmer, "The purification of bovine thrombin by affinity chromatography on benzamidine-agarose," Hoppe Seyler's Z Physiol Chem., (May 1972), vol. 353, pp. 810-814.

Segel, "How to solve mathematical problems in general biochemsitry," Biochemical Calculations, $2^{nd}$ Edition (1976), pp. 83-85.

Semba et al., "Iliofemoral deep venous thromosis: Aggressive therapy with catheter-directed thrombolysis," Radiology, (1994), vol. 191, pp. 487-494.

Uflacker R, et al., "Treatment of thrombosed dialysis access grafts: Randomized trial of surgical thrombectomy versus mechanical thrombectomy with the amplatz device[1]," JVIR, (1996), vol. 7, No. 2, pp. 185-192.

Walker, B., et al., "Strategies for the inhibition of serine proteases," CMLS. Cell. Mol. Life Sci., vol. 58, (2001), pp. 596-624.

Whisenant, B. K., et al., "Rheolytic thrombectomy with the possis AngioJet®: Technical considerations and Initial clinical experience," J. of Invasive Cardiology, vol. 11, No. 7, (Jul. 1999), pp. 421-426.

Zeit, R M., "Arterial and venous embolization: Declotting of dialysis shunts by direct injection of streptokinase[1]," Radiology, (1986), vol. 159, No. 3, pp. 639-641.

Aronen, H.J, et al., "99mTc-plasmin test in deep vein thrombosis of the leg," Eur J Nucl Med, 10:10-12 (1985).

Browse, N., "Deep Vein Thrombosis," British Medical Journal, 4:676-678 (1969).

Burnouf-Radosevich et al., "Nanofiltration, A New Specific Virus Elimination Method Applied to High-Purity Factor IX and Factor XI Concentrates," Vox Sang 67(2): 132-8 (1994) (abstract only).

Dahl, 0.E., et al., "99mTc-Plasmin Uptake Test is Unreliable for Diagnosing Asymptomatic Deep Vein Thrombosis After Hip Replacement Surgery," Thrombosis Research, 62:781-784 (1991).

Database WPI Section Ch, Week 199325 Thomson Scientific, London, GB Class B04, AN 1993-203634 XP002285931; RO103682A (Cantacuzino Inst Bucuresti) (Dec. 1991).

Edenbrandt, C.M., et al., "Comparison between 99Tcm-porcine plasmin and 99Tcm-labelled erythrocytes in diagnosis of deep vein thrombosis," Clinical Physiology 4:243-252 (1984).

Edenbrandt, C.M., et al., "Diagnosis of Deep Venous Thrombosis by 99mTc-Human Serum Albumin Microcolloid," Eur J Nucl Med 8:332-334 (1983).

Edenbrandt, C.M., et al., "Follow-up of circulatory changes secondary to deep venous thrombosis with special regards to radionuclide tests," Clinical Physiology 6:153-161 (1986).

Edenbrandt, C.M., et al., "Return to normal of 99mTc-plasmin test after deep venous thrombosis and its relationship to vessel wall fibrinolysis," Eur J Nucl Med 12:197-200 (1986).

Haidacher, D., et al., "Temperature effects in hydrophobic interaction chromatography," Proc Natl Acad Sci USA 93:2290-2295 (1996).

Ito, et al., "Separation of Human Glu-Plasminogen, Lys-Plasminogen and Plasmin by High-Performance Affinity Chromatography on Asahipak GS Gel Coupled with p-Aminobebnzamidine," Journal of Chromatography, 348: 199-204 (1985).

GE Healthcare—Affinity chromatography (Data File 18-1139-38 AC—first published Sep. 2000).

Knight, L.C., "Radiopharmaceuticals for Thrombus Detection," Seminars in Nuclear Medicine, 20(1):52-67 (1990).

Lagerstedt, C., et al., "99mTc plasmin in 394 consecutive patients with suspected deep venous thrombosis," Eur J Nucl Med, 15:771-775 (1989).

Marder, V.J., et al., "Plasmin Induces Local Thrombolysis without Causing Hemorrhage: A Comparison with Tissue Plasminogen Activator in the Rabbit," Thromb Haemost, 86:739-745 (2001).

Milne, R.M., et al., "Postoperative Deep Venous Thrombosis: A Comparison of Diagnostic Techniques," Lancet, 2 (7722):445-447 (1971).

Perrson, B. and Darte, L., "Labeling Plasmin with Technetium-99m for Scintigraphic Localization of Thrombi," International Journal of Applied Radiation and Isotopes, 28:97-104 (1977).

Rasmussen, A., et al., "Distinction by Radioisotope Technique of a Subgroup with Increased Thrombophilic Potential among Patients Submitted to Major Abdominal Surgery," Journal of Medicine, 17(5-6):357-364 (1986).

Sakata, Y., et al. "Differential binding of plasminogen to crosslinked and noncrosslinked fibrins: its significance in hemostatic defect in factor XIII deficiency, " Blood, 63:1393-1401 (1984).

Suenson, E. and Thorsen, S., "Secondary-site binding of Glu-plasmin, Lys-plasmin and miniplasmin to fibrin," Biochem. J., 197:619-628 (1981).

Tengborn, L., et al., "Demonstration of 99m-Tc-Labelled Plasmin on the Surface of Ex Vivo Thrombi," Thrombosis Research, 28:783-791 (1982).

Vali, Z. and Patthy, L., "The Fibrin-binding Site of Human Plasminogen," Journal of Biological Chemistry, 269 (22):13690-13694 (1984).

REVERSIBLY INACTIVATED ACIDIFIED PLASMIN

REFERENCE TO RELATED APPLICATION

This application is a division of U.S. patent application Ser. No. 10/143,112, filed May 10, 2002, incorporated herein fully by reference, which in turn is a continuation of International Application PCT/US00/31090, filed Nov. 13, 2000, and published in English on May 25, 2001, which in turn is a continuation-in-part of U.S. patent application Ser. No. 09/438,331, filed 13 Nov. 1999 now U.S. Pat. No. 6,355,243.

FIELD OF THE INVENTION

The present invention relates generally to compositions useful in thrombolytic therapy. More particularly, the present invention is directed to novel compositions comprising reversibly inactivated acidified serine protease compositions useful in clot dissolution therapy wherever directed delivery to a thrombus is feasible.

BACKGROUND

The blood clotting process, as a mechanism of hemostasis or in the generation of a pathological condition involving thrombi, requires two cooperating pathways: 1) following activation, triggered by the enzyme thrombin, circulating platelets adhere to one another accompanied by the release of factors like thromboxane A2 and the subsequent formation of a plug created from the aggregated platelets, and 2) the activation of a cascade of proteolytic enzymes and cofactors, most of which are plasma glycoproteins synthesized in the liver, to produce a thrombus. Thrombi are composed mainly of an insoluble fibrin network, which entraps circulating blood cells, platelets, and plasma proteins to form a thrombus.

Thromboembolic disease, i.e., the pathological blockage of a blood vessel by a blood clot, is a significant cause of mortality and morbidity. Most spontaneously developing vascular obstructions are due to the formation of intravascular blood clots, or thrombi. Small fragments of a clot may also detach from the body of a clot and travel through the circulatory system to lodge in distant organs and initiate further clot formation. Myocardial infarction, occlusive stroke, deep venous thrombosis (DVT) and peripheral arterial disease are well-known consequences of thromboembolic phenomena.

Plasminogen activators are currently the favored agents employed in thrombolytic therapy, all of which convert plasminogen to plasmin and promote fibrinolysis by disrupting the fibrin matrix (Creager M. A. & Dzau V. J., Vascular Diseases of the Extremities, ppgs. 1398-1406 in Harrison's Principles of Internal Medicine, $14^{th}$ ed., Fauci et al, editors, McGraw-Hill Co., New York, 1998; the contents of which is incorporated herein by reference in its entirety). The most widely used plasminogen activators include a recombinant form of tissue-type plasminogen activator (tPA), urokinase (UK) and streptokinase (SK), as well as a new generation of plasminogen activators selected for improved pharmacokinetics and fibrin-binding properties. All of these plasminogen activators, however, act indirectly to effect lysis and require an adequate supply of their common substrate, plasminogen, at the site of the thrombus.

UK and tPA convert plasminogen to plasmin by cleaving the $Arg^{561}$-$Val^{562}$ peptide bond. The resulting two polypeptide chains of plasmin remain joined by two interchain disulfide bridges. The light chain of 25 kDa carries the catalytic center and is homologous to trypsin and other serine proteases. The heavy chain (60 kDa) consists of five triple-loop kringle structures with highly similar amino acid sequences. Some of these kringles contain so-called lysine-binding sites that are responsible for plasminogen and plasmin interaction with fibrin, α2-antiplasmin or other proteins. Variant forms of truncated plasmin, including variants lacking some or all of the kringle regions of the plasmin heavy chain, are disclosed by Wu et al. in U.S. Pat. No. 4,774,087, incorporated herein by reference in its entirety. SK and staphylokinase activate plasminogen indirectly by forming a complex with plasminogen, which subsequently behaves as a plasminogen activator to activate other plasminogen molecules by cleaving the arginyl-valine bond.

Plasmin is a different mechanistic class of thrombolytic agent that does not activate plasminogen. Plasmin directly cleaves fibrin in a thrombus, resulting in lysis. This avoids the requirement for plasminogen or plasminogen activators to be present in a thrombus. Many clots that are deficient in plasminogen due to thrombus contraction triggered by platelets and by Factor VIII.

Although tPA, SK and UK have been successfully employed clinically to reduce a thrombotic occlusion, serious limitations persist with their use in current thrombolytic therapy. For example, because the systemic administration of tPA is not specifically targeted to the thrombus, it can result in significant systemic hemorrhage. Other limitations associated with plasminogen activators impact their overall usefulness. At best, the use of current thrombolytic therapy results in restored vascular blood flow within 90 minutes in only about 50% of patients, while acute coronary re-occlusion occurs in roughly 10% of the patients. Coronary recannulization requires on average 45 minutes or more, and intracerebral hemorrhage occurs in 0.3% to 0.7% of patients. Residual mortality is still about 50% of the mortality level in the absence of thrombolysis treatment.

A different approach that avoids many of the problems associated with the systemic administration of a plasminogen activator is to generate plasmin at the site of the thrombus or to directly administer the plasmin either into or proximally to the thrombus. Reich et al. in U.S. Pat. No. 5,288,489 discloses a fibrinolytic treatment that includes parenteral administration of plasmin into the body of a patient. The concentration and time of treatment were sufficient to allow active plasmin to attain a concentration at the site of an intravascular thrombus that is sufficient to lyse the thrombus or to reduce circulating fibrinogen levels. Reich et al. require generation of the plasmin from plasminogen immediately prior to its introduction into the body.

In contrast, Jenson in U.S. Pat. No. 3,950,513 discloses a porcine plasmin preparation that is asserted to be stabilized at low pH. However, such plasmin solution must be neutralized before systemic administration to humans for thrombolytic therapy.

Yago et al. in U.S. Pat. No. 5,879,923 discloses plasmin compositions employed as a diagnostic reagent. The compositions of Yago et al. consist low concentrations of plasmin at a neutral pH and an additional component that may be 1) an oligopeptide consisting of at least two amino acids, or 2) at least two amino acids, or 3) a single amino acid and a polyhydric alcohol, and the amino acids are specifically identified.

Numerous technical problems, such as the difficulty of preparing plasmin free of contaminating plasminogen activators, have prevented clinical use of plasmin. Plasmin preparations were typically extensively contaminated by the plasminogen activators streptokinase and urokinase, resulting in the attribution of thrombolytic activity to the contaminating plasminogen activators rather than to plasmin itself. The contaminating plasminogen activators can also trigger systemic bleeding at sites other than the targeted thrombosis. One factor limiting clinical use of plasmin is that plasmin, as a serine protease with broad specificity, is highly prone to auto-degradation and loss of activity at physiological pH when prepared as a highly purified and highly concentrated solution. This provides severe challenges to the production of high-quality plasmin, to the stable formulation of this active protease for prolonged periods of storage prior to use, and to safe and localized administration of plasmin to human patients suffering from occlusive thrombi.

Thus, there is a need for a therapeutic composition comprising a stabilized serine protease capable of cleaving fibrin and a pharmaceutically acceptable carrier with a pH range sufficiently low to reversibly inactivate the serine protease, yet sufficiently high to limit acid hydrolysis of peptide bonds within the serine protease. Further, there is a need for such therapeutic composition to have a low buffer capacity to maintain low pH during storage, yet permit plasmin to rapidly revert to its active form at the pH in the local environment of the clot.

There is also a need for a therapeutic composition comprising a reversibly inactivated acidified serine protease stabilized by at least one pharmaceutically acceptable stabilizing agent and a pharmaceutically acceptable carrier.

These and other objectives and advantages of the invention will become fully apparent from the description and claims that follow or may be learned by the practice of the invention.

SUMMARY OF THE INVENTION

This invention overcomes the disadvantages of the prior art by providing a fibrinolytic composition which can be therapeutically administered directly at or proximal to a site of a thrombotic occlusion. Further, the fibrinolytic composition of the present invention has a substantially long-term shelf life with respect to the prior art.

In one aspect of the present invention, the fibrinolytic composition comprises a reversibly inactivated acidified serine protease substantially free of a plasminogen activator, a low buffering capacity buffer, and optionally, a stabilizing agent. Such serine proteases include trypsin, chymotrypsin, pancreatic elastase II, cathepsin G, prostate-specific antigen, leukocyte elastase, chymase, tryptase, acrosin, human tissue kallikrein, and plasmin. Plasmin includes Glu-plasmin or Lys-plasmin, derivatives and modified or truncated variants thereof, including, but not limited to, midi-plasmin, mini-plasmin, or micro-plasmin.

In another aspect of the invention, the fibrinolytic composition of the present invention comprises a reversibly inactivated acidified plasmin substantially free of a plasminogen activator, a low buffering capacity buffer, and optionally, a stabilizing agent. Plasmin includes Glu-plasmin or Lys-plasmin, derivatives and modified or truncated variants thereof, including, but not limited to, midi-plasmin, mini-plasmin, or micro-plasmin.

Buffers employed in the present invention include such low buffering capacity buffers which are present in the composition at a concentration at which the pH of the composition is rapidly raised to a neutral pH by adding no more than about an equal volume of serum to the composition. In one aspect of the invention, the buffer comprises at least one pharmaceutically acceptable acid, such as an amino acid, a derivative of the at least one amino acid, a dipeptide, an oligopeptide which includes the at least one amino acid, and combinations thereof. Amino acids employable as the buffer include serine, threonine, methionine, glutamine, glycine, isoleucine, valine, aspartate, and alanine. Other low buffering capacity acids may be employed and include formic acid, acetic acid, citric acid, hydrochloric acid, lactic acid, malic acid, tartaric acid, benzoic acid, derivatives thereof, and combinations thereof. The amino acids and the other low buffering capacity acids may be combined in any desired combination as well.

Stabilizing agents which may be employed in the present invention include pharmaceutically acceptable carbohydrates, salts, glucosamine, thiamine, niacinamide, citrulline, and combinations thereof.

Thus, a unique fibrinolytic composition is now provided that successfully addresses the shortcomings of existing compositions and provides distinct advantages over such compositions. Additional objects, features, and advantages of the invention will become more apparent upon review of the detailed description set forth below when taken in conjunction with the accompanying drawing figures, which are briefly described as follows.

DETAILED DESCRIPTION

Figure 1:
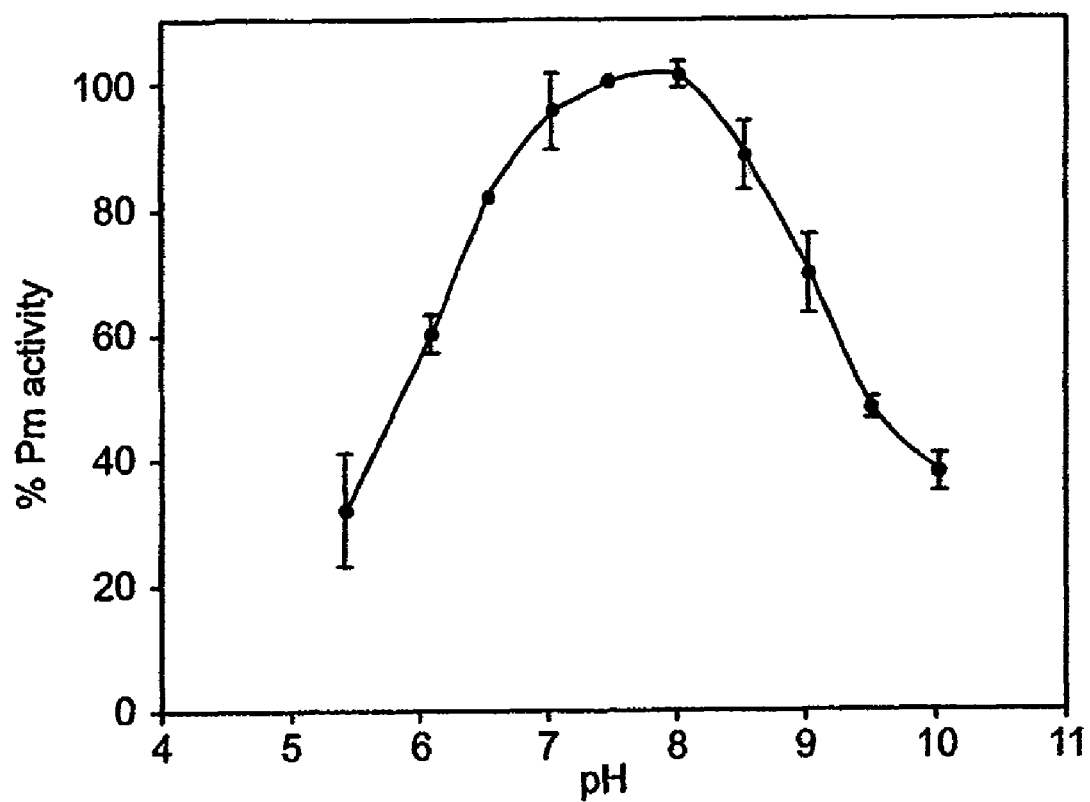
FIG. 1 illustrates the pH dependence of plasmin activity as measured with the chromogenic substrate S2251.

A full and enabling disclosure of the present invention, including the best mode known to the inventors of carrying out the invention is set forth more particularly in the remainder of the specification, including reference to the Examples. This description is made for the purpose of illustrating the general principles of the invention and should not be taken in the limiting sense.

The present invention addresses the need for a fibrinolytic composition that is stable on storage and can be therapeutically administered to a patient having a thrombotic occlusion. Therefore, in one aspect the present invention provides a fibrinolytic composition comprising a reversibly inactivated acidified serine protease substantially free of a plasminogen activator, a low buffering capacity buffer, and optionally, a stabilizing agent. Such serine proteases include trypsin, chymotrypsin, pancreatic elastase II, cathepsin G, prostate-specific antigen, leukocyte elastase, chymase, tryptase, acrosin, human tissue kallikrein, and plasmin. Plasmin includes Glu-plasmin or Lys-plasmin, derivatives and modified or truncated variants thereof, including, but not limited to, midi-plasmin, mini-plasmin, or micro-plasmin.

The present invention further provides a fibrinolytic composition comprising a reversibly inactivated acidified serine protease substantially free of plasminogen activator and a pharmaceutically acceptable acidified carrier, further comprising a pharmaceutically acceptable stabilizing agent.

In another aspect of the present invention, the fibrinolytic composition of the present invention comprises a reversibly inactivated acidified plasmin substantially free of a plasminogen activator, a low buffering capacity buffer, and optionally, a stabilizing agent. Again, plasmin includes Glu-plasmin or Lys-plasmin, derivatives and modified or truncated variants thereof, including, but not limited to, midi-plasmin, mini-plasmin, or micro-plasmin.

Buffers employed in the present invention include such low buffering capacity buffers which are present in the composition at a concentration which would allow the pH of the composition to be changed to a physiological pH by contacting body fluids. In an aspect of the invention, the buffer comprises at least one pharmaceutically acceptable acid, such as an amino acid, a derivative of the at least one amino acid, a dipeptide, an oligopeptide which includes the at least one amino acid, and combinations thereof. Amino acids employable as the buffer include serine, threonine, methionine, glutamine, alanine, glycine, isoleucine, valine, aspartate, alanine, and combinations thereof. Other low buffering capacity acids may be employed and include formic acid, acetic acid, citric acid, hydrochloric acid, lactic acid, malic acid, tartaric acid, benzoic acid, derivatives thereof, and combinations thereof. The amino acids and the other low buffering capacity acids may be combined in any desired combination as well.

Stabilizing agents which may be employed in the present invention include pharmaceutically acceptable carbohydrates, salts, glucosamine, thiamine, niacinamide, citrulline, and combinations thereof. Further stabilizing agents include, but are not limited to, monosacchrides, disaccharides, polysacchrides, polyhydric alcohols, or combinations thereof. For example, such stabilizing agents include sugars or sugar alcohols, such as glucose, maltose, mannitol, sorbitol, sucrose, lactose, trehalose, or combinations thereof. Salts, such as sodium chloride, potassium chloride, magnesium chloride, calcium chloride, or combinations thereof, are employable as stabilizing agents in the present invention.

With the escalating use of arterial and venous catheters in the clinics, local delivery of an active plasmin in close proximity to, or actually into, a thrombus offers an attractive therapeutic opportunity in thrombolytic therapy. Being an active serine protease, plasmin is a direct thrombus-dissolving agent, in contrast to plasminogen activators that require the presence of the zymogen plasminogen in the vicinity of the thrombus. Local catheter-directed thrombolytic therapy with active plasmin can be regulated to achieve total thrombolysis, and plasmin has the potential to be a safer thrombolytic agent because the lower dosage required for local delivery may significantly reduce bleeding complications frequently associated with high dose thrombolytic therapy induced by plasminogen activators. Furthermore, any potential spillage of plasmin from the immediate vicinity of the thrombus site will be quickly neutralized by circulating $\alpha_2$-antiplasmin.

In the past, there have been several technical challenges associated with plasmin purification, and storage, as well as with its therapeutic use and delivery. Plasmin is an active serine protease and is subject to autodigestion and inactivation at a physiological pH. Plasmin degradation, unfortunately, is also most evident in the pH range required for in vivo thrombolysis.

The fibrinolytic composition, as incorporated into the present invention, includes the maintenance of the plasmin in an acidic buffer during purification, as well as its formulation in an acidified carrier having a pharmaceutically acceptable low buffering capacity buffer, thereby providing a reversibly inactivated acidified plasmin-containing fibrinolytic composition substantially free of plasminogen activator. It is contemplated to be within the scope of the present invention for the fibrinolytic composition to be a lyophilized composition that may be reconstituted by the addition of a pharmaceutically acceptable carries such as, but not limited to, water, physiological saline or any other solvent that will allow administration of the composition to a human or animal. Its efficacy in restoring vascular patency was demonstrated in in vitro assays and in an in vivo rabbit jugular vein thrombolysis model.

The term "reversibly inactivated" as used herein refers to an enzymatic activity that is substantially free of activity under a specific set of conditions but will revert to an active form when transferred to another set of conditions.

The term "pharmaceutically acceptable carrier" as used herein refers to any carrier that is physiologically tolerated by a recipient human or animal, including, but not limited to, water, salt solutions, physiological saline, or any other liquid or gel in which a fibrinolytic agent such as plasmin may be dissolved or suspended. The "pharmaceutically acceptable carrier" may include any pharmaceutically acceptable compound that will give a plasmin solution having a pH below about 4.0 and which has low or zero buffering capacity.

The term "physiological pH" as used herein refers to a pH between about pH 6.5 and about 7.5, ore typically between about pH 7.1 and about 7.5.

The term "body fluid" as used herein refers to any body fluid including, but not limited to, blood, serum, plasma, semen and urine.

The term "low pH buffering capacity buffer" or "low buffering capacity buffer" as used herein refers to the amount of acid or base that a buffer can neutralize before the pH begins to change to an appreciable degree. As used herein a low buffering capacity buffer will be significantly pH adjusted by the addition of a small volume of an acid or base relative to the volume of the low buffering capacity buffer solution. For example, in the present invention, the buffer is present in the composition at a concentration that would allow the pH of the composition to be changed by contacting a body fluid. This term is meant to include solutions acidified by strong acids including, but not limited to, hydrochloric acid, nitric acid and sulfuric acid, and which have no buffering capacity.

The term "thrombus" as used herein refers to a thrombus in a blood vessel or device contacting blood (e.g. catheter devices or shunts). A thrombus may comprise fibrin and may further comprise, but is not limited to, platelets, erythrocytes, lymphocytes, lipid or any combination thereof. A "thrombus" may be, but is not limited to, an annular thrombus, ball thrombus, hyaline thrombus, mural thrombus, stratified thrombus or white thrombus.

The term "thrombotic occlusion" as used herein refers to a partial or total blockage of a vessel due to the formation of a thrombotic clot, wherein the thrombus comprises at least fibrin. The vascular vessel occluded may be, but is not limited to, a vein, artery, venule, arteriole, capillary, vascular bed or the heart and may be Within any vascularized organ or tissue of the human or animal body. The thrombotic occlusion may also be of a catheter or other implant including, but not limited to, prosthetic vessels and grafts of synthetic, human or animal origin and effectively blocked by an occlusion comprising fibrin.

The term "catheter device" as used herein refers to any catheter or tube-like device that may enter the body, and includes but is not limited to, an arterial catheter, cardiac catheter, central catheter, central venous catheter, intravenous catheter, peripherally inserted central catheter, pulmonary artery catheter or tunneled central venous catheter and arterio-venal shunts.

The term "pharmaceutically acceptable acidified carrier" as used herein refers to any pharmaceutically acceptable carrier that has been acidified to a pH below about 4.0.

The "pharmaceutically acceptable acidified carrier" may comprise a low or zero buffering capacity buffer such as a carboxylic acid such as, but not limited to, formic acid, acetic, proprionic, butyric, citric, succinic, lactic or malic acids acidified to a pH below about 4.0 by the addition of an inorganic acid; or at least one amino acid such as, but not limited to, glycine, alanine, valine, isoleucine, threonine or glutamine, methionine, serine, aspartic acid or at least one inorganic acid such as, but not limited to, sulfuric acid, hydrochloric acid, nitric acid or phosphoric acid or any combination thereof. It is contemplated to be within the scope of the present invention for the acid moiety of the pharmaceutical carrier to be at least one physiologically tolerated buffer, oligopeptide, inorganic or organic ion or any combination thereof that will maintain a pH in the pharmaceutically acceptable carrier below a value of about 4.0.

The term "carbohydrate" as used herein refers to any pharmaceutically acceptable saccharide or disaccharide such as, but not limited to, glucose, fructose, maltose, sucrose, lactose, trehalose, mannose, sugar alcohols including, but not limited to, sorbitol and mannitol, and polysaccharides such as, but not limited to, dextrins, dextrans, glycogen, starches and celluloses, or any combination or derivative thereof that are pharmaceutically acceptable to a human or animal.

The term "stabilizing agent" as used herein refers to at least one compound such as, but not limited to, polyhydric alcohols, glycerol, ascorbate, citrulline, niacinamide, glucosamine, thiamine, or inorganic salt such as, but not limited to, sodium chloride, potassium chloride, calcium chloride, magnesium chloride or manganese chloride or any combination thereof that will increase the stability of a preparation of plasmin.

The term "reversibly inactivated acidified plasmin" as used herein refers to any catalytically active form of plasmin capable of proteolytically cleaving fibrin when under physiological conditions, but reversibly inactivated when placed at a pH between about pH 2.5 to about 4.0. The term "inactivated" as used herein refers to a total or substantial reduction in enzymic activity compared to the activity at physiological pH. The term "active plasmin" as used herein refers to a plasmin under conditions where the plasmin is capable of proteolytically cleaving fibrin. The term "plasmin" includes, but is not limited to Glu-plasmin, Lys-plasmin, derivatives, modified or truncated variants thereof. The term "truncated variants" includes, but is not limited to, midi-plasmin, mini-plasmin or the micro-plasmin as disclosed in U.S. Pat. No. 4,774,087 incorporated herein by reference in its entirety.

The term "anti-coagulant" as used herein refers to any compound capable of inhibiting the formation of a thrombus including, but not limited to, hiruidin, heparin, thrombin inhibitors, platelet inhibitors, and any derivatives or combinations thereof.

The term "serine protease" as used herein refers to any serine protease capable of proteoytically cleaving fibrin including, but not limited to, plasmin, trypsin, chymotrypsin, pancreatic elastase II, cathepsin G, prostate-specific antigen, leukocyte elastase, chymase, tryptase, acrosin and human tissue kallikrein.

One limitation of current thrombolytic therapy with plasminogen activators is plasminogen availability surrounding or within a thrombus. The local delivery of a fibrinolytic agent to a thrombus now allows plasmin itself to be a potent therapeutic agent directly administered to a thrombus. In contrast to various plasminogen activators that are currently used as thrombolytics, direct localized thrombolytic therapy with plasmin can be intensified to whatever level is required to achieve clot lysis. This is because plasmin acts directly upon the fibrin polymer. Also, plasmin, when delivered directly into or adjacent to a thrombus, allows a lower effective dose to be administered with a concomitant reduction in the systemic hemorrhage typically associated with conventional thrombolytic therapy. Excess plasmin can also be rapidly inactivated by circulating $\alpha$2-antiplasmin.

The present invention contemplates that plasmin may be produced from plasminogen using any method that will yield a purified active plasmin substantially free of plasminogen activator. It is within the scope of the present invention for the plasminogen to be any recombinant plasminogen or a truncated plasminogen such as, but not limited to, the mini-plasminogen and micro-plasminogen, as disclosed by Wu et al. in U.S. Pat. No. 4,774,087 incorporated herein by reference in its entirety. For example, Examples 1 and 2 below disclose a method whereby active plasmin was prepared from plasminogen purified from Cohn Fraction II+III. The purity of the plasmin obtained using this method was greater than 95% and the specific activity was in the range of 18-23 CU/mg. The plasmin preparations were substantially free of urokinase, or any other plasminogen activator used for conversion of plasminogen into plasmin.

The plasmin of the present invention was purified by binding to a benzamidine affinity column and the subsequently eluted plasmin was collected and stored in an acidified pharmaceutically acceptable carrier. Results showed that a low pH in the range of about 2.5 to about 4.0 greatly stabilized the plasmin composition, even when held at room temperature or greater. While not bound by any one theory, it is believed that at this low pH the plasmin has minimal serine protease activity that would otherwise lead to autodegradation, as is seen when plasmin is stored at physiological pH of between about 7.0 to about 7.5.

When the plasmin is administered directly into a thrombus, or proximal thereto, the plasmin encounters the physiological pH of the clot of about 7.4. The acidified pharmaceutically acceptable carrier attains the pH value of the thrombus, whereupon the plasmin recovers its serine protease activity and begins to digest fibrin. Furthermore, the high concentration of fibrin within the thrombus provides an alternative substrate for the plasmin to minimize auto-degradation and maximize thrombolysis.

Fibrinolytic therapy employing a plasmin preparation that renders plasmin proteolytically inactive until administered into, or immediately adjacent to, a thrombus and which is also substantially free of any plasminogen activator reduces the likelihood of undesirable systemic hemorrhage. Excess administered plasmin is rapidly inactivated by circulating serum inhibitors such as $\alpha_2$-antiplasmin, and the plasminogen activators that would otherwise circulate to induce distal fibrinolysis are substantially absent.

Reversibly inactivated acidified plasmin, of the present invention may be readily stored, even at 37° C., in low buffering capacity pharmaceutically acceptable carriers such as, but not limited to, 2 mM sodium acetate. Any pharmaceutically acceptable moiety may be used, singularly or in combination that maintains the composition at a pH in the range of about 2.5 to about 4.0, especially at a pH of about 3.1 to about pH 3.5. Acidic compounds useful in the present invention, either singly or any combination thereof, include but are not limited to formic acid, acetic acid, citric acid, hydrochloric acid, a carboxylic acid such as, but not limited to, lactic acid, malic acid, tartaric acid, benzoic acid, serine, threonine, methionine, glutamine, glycine, isoleucine, valine, alanine, aspartic acid, derivatives thereof, or combinations thereof that will maintain the pH in the pharmaceutically acceptable carrier between about pH 2.5 to about pH 4.0.

The reversibly inactivated acidified plasmin composition of the present invention may further comprise at least one stabilizing agent such as a pharmaceutically acceptable carbohydrate including, but not limited to, monosaccharides, disaccharides, polysaccharides, and polyhydric alcohols. For example, pharmaceutically acceptable carbohydrate stabilizers contemplated to be within the scope of the present invention include sugars such as, but not limited to, sucrose, glucose, fructose, lactose, trehalose, maltose and mannose, and sugar alcohols including, but not limited to, sorbitol and mannitol. Contemplated within the scope of the present invention are polysaccharides such as, but not limited to, dextrins, dextrans, glycogen, starches and celluloses, or any combination thereof pharmaceutically acceptable to a human or animal patient.

Stabilizing agents contemplated as within the scope of the present invention and useful in stabilizing the reversibly inactivated acidified plasmin composition of the present invention include, but are not limited to, glycerol, niacinamide, glucosamine, thiamine, citrulline and inorganic salts such as, but not limited to, sodium chloride, potassium chloride, magnesium chloride, calcium chloride, or any combination thereof. Other stabilizing agents contemplated as within the scope of the present invention may include, but are not limited to, pharmaceutically acceptable compounds such as benzyl alcohol or benzoic acid, to retard microbial contamination.

A plasmin composition according to the present invention can be administered by any method that will deliver the plasmin as a bolus or as a prolonged infusion directly into a thrombus, or to a site a short distance proximal to the thrombus whereupon the plasmin composition can rapidly encounter the thrombus. By minimizing the distance from the catheter to the thrombus, the reversibly inactivated acidified plasmin composition's exposure to serum inhibitors is reduced. Catheter delivery to a thrombus allows precision in placing the plasmin composition, especially within the thrombus.

A description of the method of treating a thrombotic occlusion in a patient using a therapeutically effective dose of the reversibly inactivated acidified plasmin compositions of the present invention is disclosed in U.S. patent application Ser. No. 10/143,157, entitled "Method of Thrombolysis by Local Delivery of Reversibly Inactivated Acidified Plasmin", commonly assigned and filed contemporaneously with the instant application, and is incorporated herein by reference in its entirety.

Additionally, a process for producing the reversibly inactivated acidified plasmin composition of the instant invention is disclosed in U.S. patent application Ser. No. 10/143,156, entitled "Process for the Production of a Reversibly Inactivated Plasmin Composition", commonly assigned and filed contemporaneously with the instant application, and is incorporated herein by reference in its entirety.

Thus, the reversibly inactivated acidified plasmin composition of the present invention can be stored without a significant loss in the activity of the plasmin restored by adjusting the pH of the composition to physiological pH and safely used as a thrombolytic agent during catheter-assisted administration to a patient having a thrombotic occlusion. The present invention is a plasmin composition substantially free of plasminogen activators that exhibits at least comparable fibrinolytic activity to tPA and the safety profile appears at least similar in this animal model of local thrombolytic delivery. It is contemplated to be within the scope of the present invention that the reversibly inactivated acidified fibrinolytic enzyme may be, but is not limited to, plasmin, derivatives of plasmin such as truncated forms thereof including, but not limited to, mini-plasmin and micro-plasmin as disclosed by Wu et al. in U.S. Pat. No. 4,774,087 incorporated herein by reference in its entirety.

The present invention is further illustrated by the following examples, that are provided by way of illustration and should not be construed as limiting. Even though the invention has been described with a certain degree of particularity, it is evident that many alternatives, modifications, and variations will be apparent to those skilled in the art in light of the present disclosure. Accordingly, it is intended that all such alternatives, modifications, and variations that fall within the spirit and the scope of the invention be embraced by the defined claims.

It should be appreciated by those of skill in the art that the techniques disclosed in the examples which follow represent techniques discovered by the inventors to function well in the practice of the invention, and thus can be considered to constitute preferred modes for its practice. Those of skill in the art should, however, in light of the present disclosure, will appreciate that many changes can be made in the specific embodiments disclosed and still obtain like or similar results without departing, again, from the spirit and scope of the present invention. The contents of all references, published patents and patents cited throughout the present application are hereby incorporated by reference in their entirety.

EXAMPLES

Example 1

Sources of Proteins Investigated

Plasminogen was purified from Cohn Fraction II+III paste by affinity chromatography on Lys-Sepharose as described by Deutsch & Mertz (1970). Thus, 200 g of the paste was resuspended in 2 liter of 0.15M sodium citrate buffer, pH 7.8. The suspension was incubated overnight at 37° C., centrifuged at 14,000 rpm, filtered through fiberglass and mixed with 500 ml of Lys-Sepharose 4B (Pharmacia). Binding of plasminogen was at room temperature for 2 hours. The Lys-Sepharose was then transferred onto a 2 liter glass filter, and washed several times with 0.15M sodium citrate containing 0.3M NaCl until the absorbance at 280 nm dropped below 0.05. Bound plasminogen was eluted with three 200 ml portions of 0.2M ε-aminocaproic acid. Eluted plasminogen was precipitated with 0.4 g solid ammonium sulfate/ml of plasminogen solution. The precipitate of crude (80-85% pure) plasminogen was stored at 4° C.

Low-molecular weight urokinase (LMW-urokinase) (Abbokinase-Abbott Laboratories, Chicago Ill.) was further purified by affinity chromatography on benzamidine-Sepharose. The Urokinase was then coupled to CNBr-activated Sepharose 4B by mixing 1.3 mg of LMW-urokinase in 50 mM acetate buffer, pH 4.5, and diluting with 5 ml of the coupling buffer, 0.1M sodium bicarbonate, pH 8.0.

This solution was immediately combined with 5 ml of CNBr-activated Sepharose previously swollen and washed in 0.1 M HCl. The coupling occurred for 4 hours on ice with shaking. The excess of the CNBr active group was blocked with 0.1M Tris, pH 8.0. Each batch of urokinase-Sepharose was used 5 times and stored in 50% glycerol in water at 4° C. between the cycles. Tissue plasminogen activator (Activase) was from Genentech. Plasminogen-free fibrinogen and α-thrombin (3793 U/ml) were from Enzyme Research, Inc. $α_2$-Antiplasmin was obtained from Athens Research Technologies. Commercially available plasmin was from Haemotologic Technologies, Inc. Chromogenic plasmin substrate S2251 was from Chromogenix. $^{125}$I-Labeled human fibrinogen (150-250 μCi/mg) was from Amersham Pharmacia Biotech. SDS-polyacrylamide gel electrophoresis was performed in the Pharmacia Phast System apparatus using premade 8-25% gradient gels and SDS-buffer strips. The source of plasminogen is not limited to purification from a plasma source. It is contemplated that plasminogen may also be obtained from a transgenic or recombinant source.

Example 2

Purification of Active Plasmin (i) Activation of Plasminogen to Plasmin Using Urokinase-Sepharose.

Plasminogen was cleaved to plasmin yielding plasmin without contamination of the final preparation by using an immobilized plasminogen activator. Urokinase cleaves plasminogen directly. Plasminogen activation by urokinase does not depend on the presence of fibrin as in the case of tPA, and urokinase is a human protein. These factors, and its relative low cost, make urokinase the preferred activator, although this does not preclude the use of tPA, streptokinase or any other cleavage means yielding an active plasmin capable of fibrin degradation. The ammonium sulfate precipitate of crude plasminogen was centrifuged at 14,000 rpm and resuspended in a minimal volume using 40 mM Tris, containing 10 mM lysine, 80 mM NaCl at pH 9.0 to achieve the final protein concentration of 10-15 mg/ml. The plasminogen solution was dialyzed overnight against the same buffer to remove ammonium sulfate. The dialyzed plasminogen solution (10-20 ml) was diluted with an equal volume of 100% glycerol and combined with 5 ml of urokinase-Sepharose. The use of 50% glycerol reduces autodegradation of plasmin during activation. Plasmin is stable in 50% glycerol and can be stored in this solution at –20° C. for an extended period.

The plasminogen activation occurred at room temperature for between 2 hours and 24 hours depending on the freshness of the urokinase-Sepharose. With a fresh batch of urokinase-Sepharose, activation could be completed in 2 hours. It deteriorates, however, and becomes less efficient after several cycles, necessitating the use of SDS-PAGE under reducing conditions to monitor the progress of plasminogen activation. Upon completion of the activation, the plasmin solution was filtered from the urokinase-Sepharose with a glass filter, and immediately applied to benzamidine-Sepharose.

(ii) Capturing of Plasmin on Benzamidine-Sepharose.

Since the plasmin is a serine protease with trypsin-like specificity, benzamidine-Sepharose is an affinity absorbent that allowed capture of the active plasmin. A plasminogen solution in 50% glycerol was applied to the 50 ml benzamidine-Sepharose column equilibrated with 0.05M Tris, pH 8.0, containing 0.5M NaCl with a flow rate of 3 ml/min. The column was run at 3 ml/min at 3-7° C. The front portion of the non-bound peak contained high-molecular weight impurities. The rest of the non-bound peak is represented by residual non-activated plasminogen and by inactive autodegradation products of plasmin.

(iii) Elution of the Bound Plasmin with Low pH Buffer.

To protect plasmin from inactivation at neutral pH conditions, acidic elution conditions were selected. The plasmin bound to benzamidine-Sepharose was eluted with 0.2M glycine buffer, pH 3.0 containing 0.5M NaCl. The bound peak was typically divided into three pools, two front peaks, B1 and B2, and the bulk of the eluted material as B3.

Non-reducing gel analysis showed that all three pools contained highly pure (>95%) plasmin. The gel analysis, however, in addition to the heavy and light chains of plasmin, revealed some low molecular weight bands in a range of 10-15 kDa as a result of partial internal cleavage degradation of the plasmin.

The front portion of peak B1 typically contained most of the low molecular weight impurities. The B2 and B3 pools were less degraded. The front portion of the bound peak had very little of the plasmin activity and was usually discarded. The loss of activity in this material may be due to autodegradation during chromatography, because there is no glycerol present in the eluted material, and the pH of the front portion is intermediate between the pH of the equilibrating and eluting buffers, typically in a range of pH 6-6.5. The eluted plasmin, substantially free of plasminogen activators, was collected in tubes containing 2M glycine buffer, pH 3.0 (10% of the collected volume).

(iv) Formulation of Eluted Material in Acidified Water (pH 3.7).

Eluted plasmin was dialyzed with water and acidified to about pH 3.7 with glacial acetic acid. Any acid providing a pharmaceutically acceptable acidified carrier having a low buffering capacity buffer and having a pH between about 2.5 to about 4.0 can be used. For example, also contemplated within the scope of this invention is the use of other acids and amino acids such as, but not limited to, inorganic acids, carboxylic acids, aliphatic acids and amino acids including, but not limited to, formic acid, acetic acid, citric acid, lactic acid, malic acid, tartaric acid, benzoic acid, serine, threonine, valine, glycine, glutamine, isoleucine, P-alanine and derivatives thereof, either singly or any combination thereof, that will maintain the pH in the pharmaceutically acceptable carrier of about 2.5 to about 4.0.

Plasmin-specific activity was measured using an adapted caseinolytic assay as described by Robbins & Summaria (1970). One ml of 4% casein solution in acidified water and an appropriate volume of 67 mM sodium phosphate buffer, pH 7.4 was added to a test polycarbonate tube. The solutions were vortexed and incubated at 37° C. for 10 minutes. Plasmin samples or buffer (blank) were added to each tube at 15 second intervals, mixed thoroughly and incubated at 37° C. for 30 minutes. The reaction was stopped with the addition of 3 ml of 15% trichloroacetic acid and the precipitate was allowed to form for 15 minutes. The tubes were centrifuged at 3200 rpm for 20 minutes. The supernatants were transferred to cuvettes and the $A_{280}$ of each sample was determined. The specific caseinolytic activity of each sample was determined by the following formula:

$$\frac{3.27 \times [A_{280}(\text{Plasmin Sample}) - A_{280}(\text{Blank})]}{\mu g \text{ Plasmin in Assay}} = CU/mg$$

The plasmin concentration was determined spectrophotometrically using the extinction coefficient of 1.7 for 0.1% solution.

Example 3 pH-dependent Stability of Plasmin

Plasmin exhibits a bell-shaped pH dependence of its catalytic activity. As shown in FIG. 1, plasmin has maximum enzyme activity at pH 7.5-8.0, and its activity rapidly decreases at either more alkaline or more acidic pHs. Plasmin is mostly inactive, and reversibly so, below pH 4.0, due to the protonation of histidine in the catalytic center, as shown by Robbins & Summaria, (1976) and Castellino & Powell (1981).

Plasmin is very unstable at a physiological pH. Both the heavy chain and light chains of plasmin degraded dramatically within hours at room temperature and 4° C. Plasmin was formulated at 1 mg/ml in 0.04M sodium phosphate, pH 7.4, and incubated at 22° C. or 4° C. for 6 hours. During the incubation, the plasmin integrity was analyzed every two hours by reducing SDS-PAGE analysis. Both the heavy chain and light chain degraded rapidly within hours at 22° C. and 4° C. as shown in Table 1.

TABLE 1

The rapid degradation of plasmin in neutral pH solution at 22° C. and 4° C.

| | | | | % of intact heavy chain | | | | % of intact light chain | | | |
|---|---|---|---|---|---|---|---|---|---|---|---|
| Plasmin | Buffer | PH | Temp | Initial | 2 hr | 4 hr | 6 hr | Initial | 2 hr | 4 hr | 6 hr |
| 1 mg/ml | 0.04M PO$_4$ | 7.4 | 22° C. | 100% | 27% | 27% | 29% | 100% | 29% | 26% | 28% |
| 1 mg/ml | 0.04M PO$_4$ | 7.4 | 4° C. | 100% | 32% | 27% | 25% | 100% | 33% | 25% | 22% |

(The intact heavy chain and light chain of plasmin at initial time point were normalized as 100%.)

Plasmin at 1 mg/ml was incubated at 37° C. for 14 days under different acidic conditions. The changes in plasmin heavy chain and light chain were analyzed by running reducing SDS-PAGE. Plasmin was formulated at 1 mg/ml in 0.04M sodium phosphate, pH 7.4 and was also incubated at 4° C. for six hours. During the incubation, the activity of the plasmin sample was measured every two hours by chromogenic potency assay. Plasmin potency was quantitatively measured using the MLA 1600C analyzer (Pleasantville, N.Y.). Plasmin hydrolyzed the chromogenic substrate S-2403 (D-pyro-glutamyl-L-Phenylalanyl-L-Lysine-p-Nitroaniline hydrochloride or abbreviated as pyro-Glu-Phe-Lys-pNA) to form peptide and the chromophoric group p-nitroaniline (pNA). The rate of color formation was measured kinetically at 405 nm. The amount of substrate hydrolyzed was proportional to the plasmin activity in the sample. A standard curve was generated from the linear regression of the rate of color formation (OD/min) versus the potency of a plasmin standard. The linear equation together with the observed rate for an unknown sample was used to calculate the potency of unknowns. The potency of plasmin was reported in units of mg/ml.

Plasmin integrity was significantly decreased by incubation at a physiological pH, as shown in Table 2.

TABLE 2

The rapid decrease of plasmin activity in neutral pH solution at 4° C.

| | | | Chromogenic Potency | | | |
|---|---|---|---|---|---|---|
| Plasmin | Buffer | pH | Initial | 2 hr | 4 hr | 6 hr |
| 1 mg/ml | PO$_4$, 0.04M | 7.4 | 100% | 43.3% | 32.6% | 26.4% |

(The activity of plasmin solution at initial time point was normalized as 100%.)
In this neutral pH solution, plasmin activity decreased more than 70% after 6 hours at 4° C.

Figure 2:
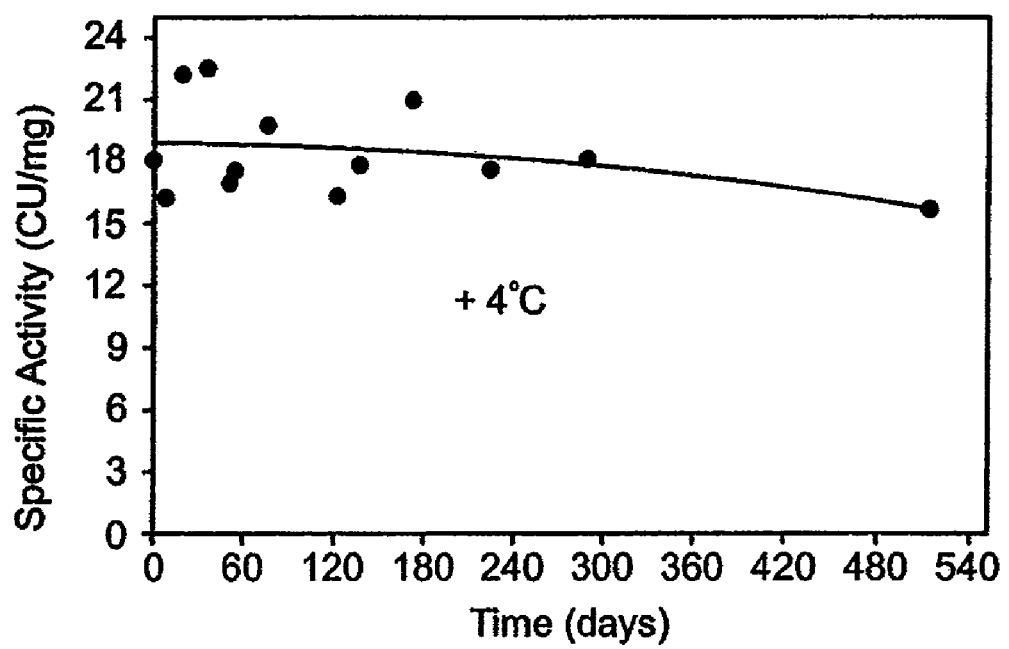
FIG. 2 illustrates plasmin stability in acidified saline (pH 3.7) as measured by a caseinolytic assay.
Figure 2:
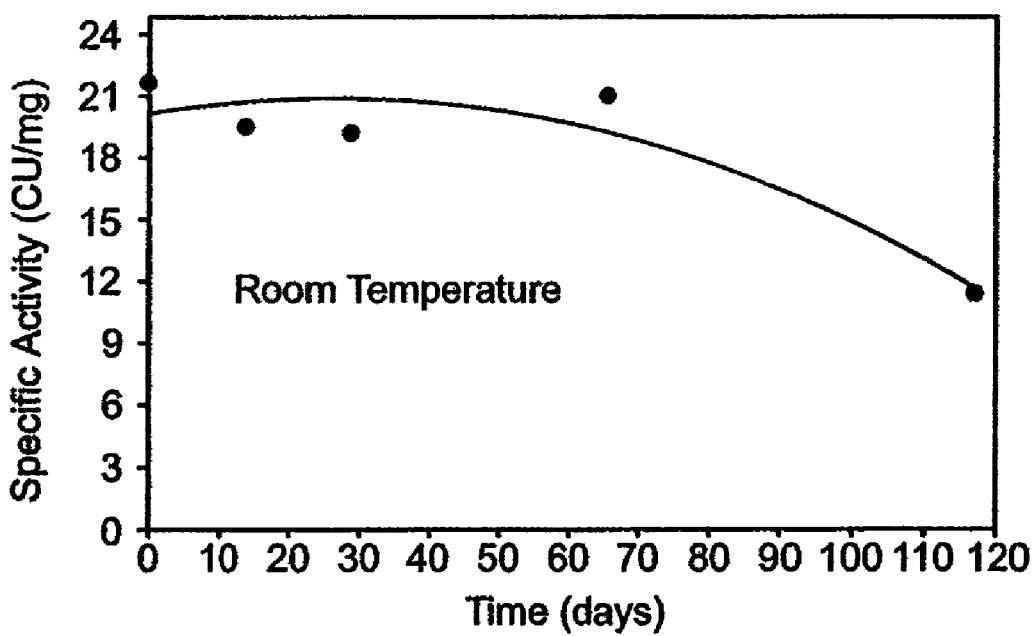

Plasmin formulated in acidified water at pH 3.7 is stable. It can be kept in this form for months at reduced temperatures without any loss of activity or the appearance of degradation products of a proteolytic or acidic nature. FIG. 2 and the data of Table 3 show the stability of plasmin at 4° C. and at room temperature.

TABLE 3

Stability of 1 mg/ml plasmin in the following acidic conditions at 37° C.

| Formulation | Plasmin (mg/ml) | Acidic Condition | pH | % intact heavy chain after 14 days at 37° C. | % intact light chain after 14 days at 37° C. |
|---|---|---|---|---|---|
| 1 | 1 | 5 mM HAC/NaAc | 2.5 | 19% | 62% |
| 2 | 1 | 5 mM HAC/NaAc | 3.0 | 41% | 92% |
| 3 | 1 | 5 mM HAC/NaAc | 3.4 | 48% | 92% |
| 4 | 1 | 5 mM HAC/NaAc | 3.4 | 49% | 96% |
| 5 | 1 | 5 mM HAC/NaAc | 3.4 | 50% | 96% |
| 6 | 1 | 5 mM HAC/NaAc | 3.7 | 13% | 123% |
| 7 | 1 | 5 mM HAC/NaAc | 4.0 | 9.3% | 107% |
| 8 | 1 | 5 mM citric acid/Na citrate | 2.27 | 9.3% | 64% |
| 9 | 1 | 5 mM citric acid/Na citrate | 3.1 | 33% | 68% |
| 10 | 1 | 5 mM citric acid/Na citrate | 3.56 | 46% | 88% |
| 11 | 1 | 5 mM citric acid/Na citrate | 4.0 | 7.4% | 104% |
| 12 | 1 | 5 mM glycine | 2.2 | 7.3% | 104% |
| 13 | 1 | 5 mM glycine | 3.1 | 36% | 70% |
| 14 | 1 | 5 mM glycine | 3.5 | 49% | 85% |
| 15 | 1 | 5 mM glycine | 3.8 | 12% | 85% |
| 16 | 1 | 5 mM glycine | 4.1 | 6% | 81% |
| 17 | 1 | 5 mM serine | 3.4 | 56% | 100% |
| 18 | 1 | 5 mM threonine | 3.4 | 54% | 100% |
| 19 | 1 | 5 mM valine | 3.4 | 52% | 96% |
| 20 | 1 | 5 mM isoleucine | 3.4 | 51% | 100% |
| 21 | 1 | 5 mM β-alanine | 3.7 | 33% | 90% |
| 22 | 1 | 2 mM benzoic acid | 3.5 | 42% | 93% |
| 23 | 1 | 2 mM lactic acid | 3.5 | 45% | 91% |
| 24 | 1 | 2 mM malic acid | 3.5 | 50% | 90% |
| 25 | 1 | 2 mM tartaric acid | 3.5 | 28% | 87% |

(The intact heavy chain and light chain in each formulation before incubation were normalized as 100%; HAc/NaAc— = acetic acid/sodium acetate)

Figure 3:
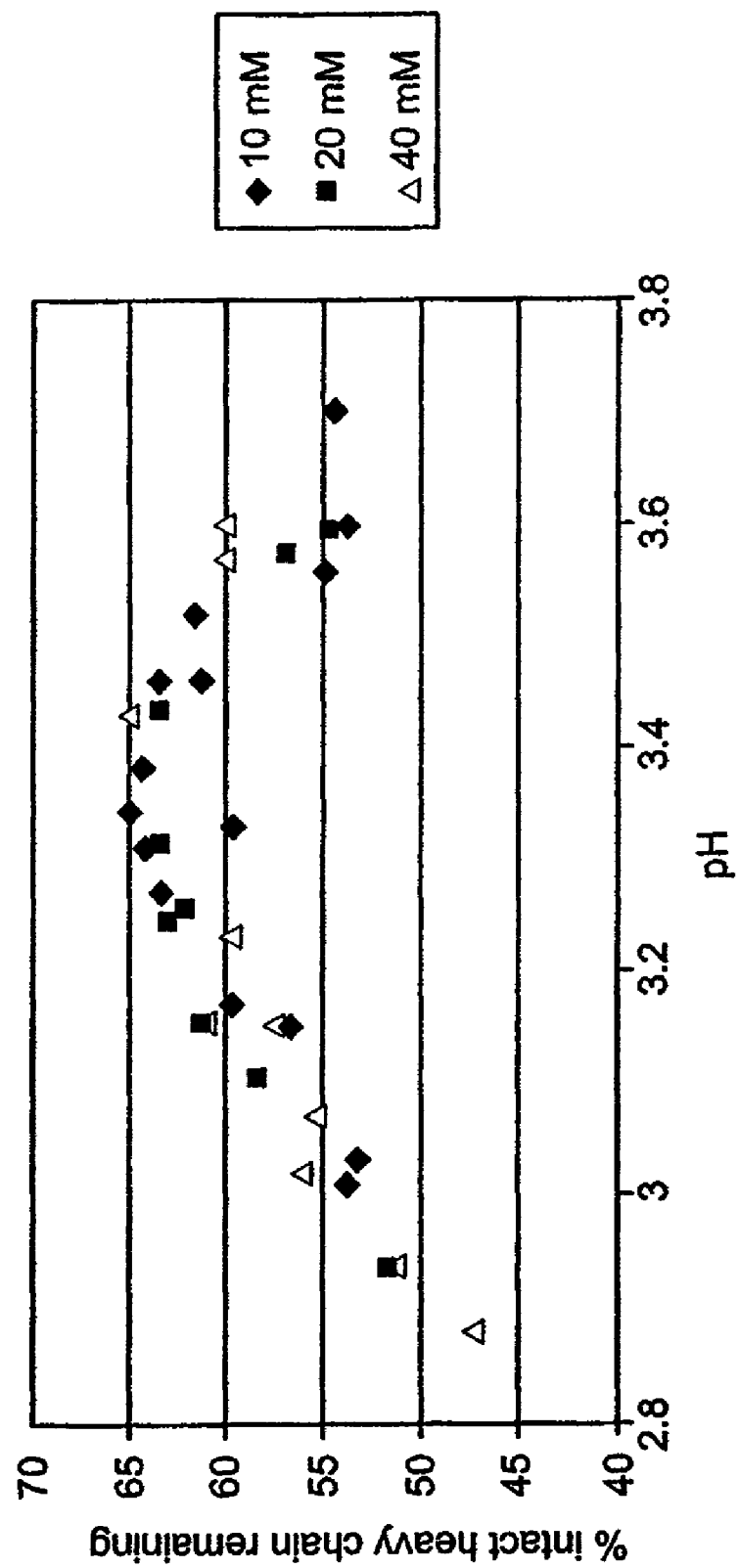
FIG. 3 illustrates that pH stability of plasmin does not depend on the buffering agent nor concentration of buffering agent.

At 4° C., plasmin is stable for at least nine months. At room temperature, reversibly inactivated acidified plasmin is stable for at least two months. To determine the optimal pH of different buffering agents and the effect of buffer concentration on plasmin stability, compositions of 1 mg/ml of plasmin were prepared in 10 mM, 20 mM or 40 mM sodium acetate or glycine at various pH values. The samples were stored at 37° C. for 7 days, and the relative amount of intact plasmin heavy chain remaining was determined by densitometry of Coomassie stained SDS gels. Shown in FIG. 3 is a plot of pH versus percent heavy chain relative to total protein in each lane of the SDS gels. The results demonstrate a pH stability optimum of about 3.1-3.5, irrespective of the type of buffer, or buffer concentration.

Long-term stability at room temperature is important because it would make this formulation compatible with long regimens of thrombolytic administration. For example, 36 hour administration of thrombolytics such as tissue plasminogen activator or urokinase is common in treatment of peripheral arterial occlusions.

The ability of reversibly inactivated acidified plasmin to become fully active upon transfer to physiological pH is evidenced by its activity in the caseinolytic assay and also in the 125'-fibrin-labeled thrombolysis assays. Both of these assays are performed at pH 7.4, and there was complete recovery of plasmin activity during the change of pH and passing through the isoelectric point (pH 5-5.5). The plasmin is formulated in a low buffering capacity solvent and, when added to a buffered solution such as plasma, it rapidly adopts the neutral or physiological pH instantly and the precipitation that usually accompanies the slow passage through the isoelectric point, does not occur.

Example 4

Figure 4:
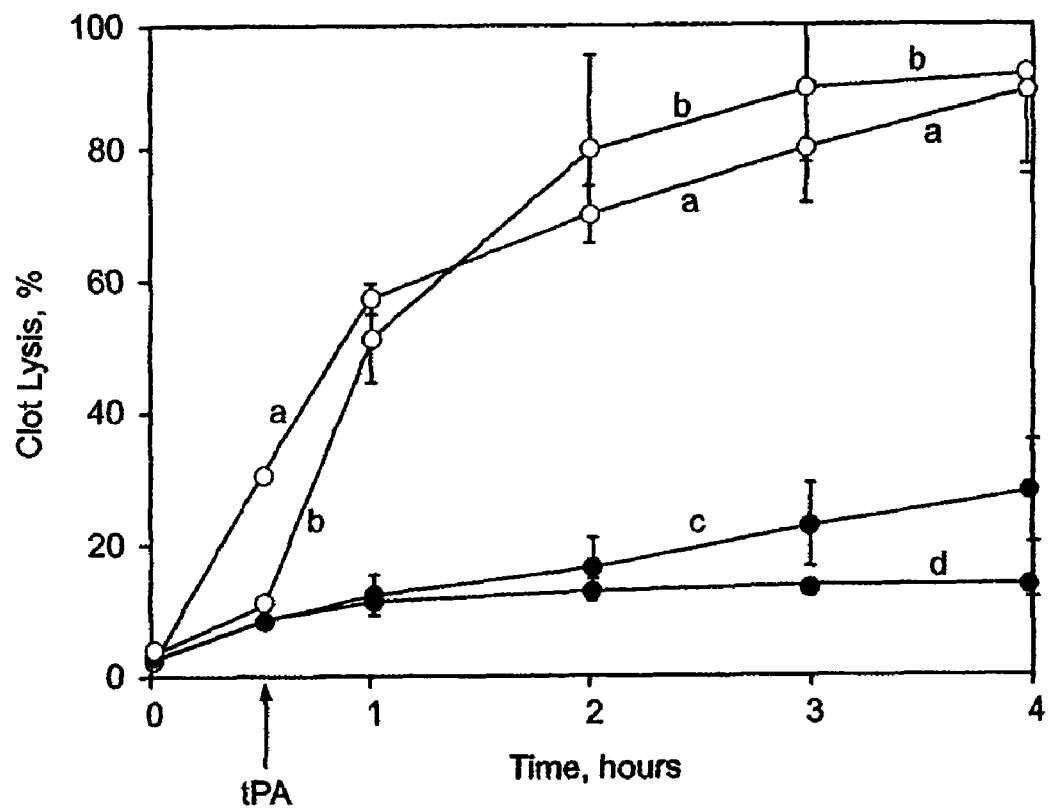
FIG. 4 illustrates the effectiveness of plasmin or tPA plus plasminogen in thrombolysis.

Plasmin has the Same Intrinsic Fibrinolytic Potency as a Plasminogen/Plasminogen Activator Mixture Plasmin has the same intrinsic fibrinolytic potency as a plasminogen/plasminogen activator mixture. Fibrinolytic potency of plasmin was compared with that of a Lys-plasminogen and tPA mixture. These experiments were performed in a defined system consisting of an $^{125}$I-radiolabeled fibrin thrombus submersed in PBS. FIG. 4 shows that, in a buffered environment, thrombolysis achieved with plasmin is almost identical to the Lys-plasminogen plus tPA mixture (curves a and b, respectively). At the same time, no thrombolysis was observed with tPA alone (curve c) or in the absence of any proteins (curve d). The data obtained with tPA alone shows that its activity is dependent on its substrate, plasminogen, to be an effective thrombolytic.

These data indicate that, in the absence of inhibitors and other protein factors present in plasma, there is no difference in the ability to lyse fibrin thrombi between purified plasmin and the combination of tPA and Lys-plasminogen. To assess the thrombolytic potency of active plasmin, the $^{125}$I-fibrin-labeled thrombolysis assay was performed with plasma thrombi in a plasma environment.

Example 5

Figure 5:
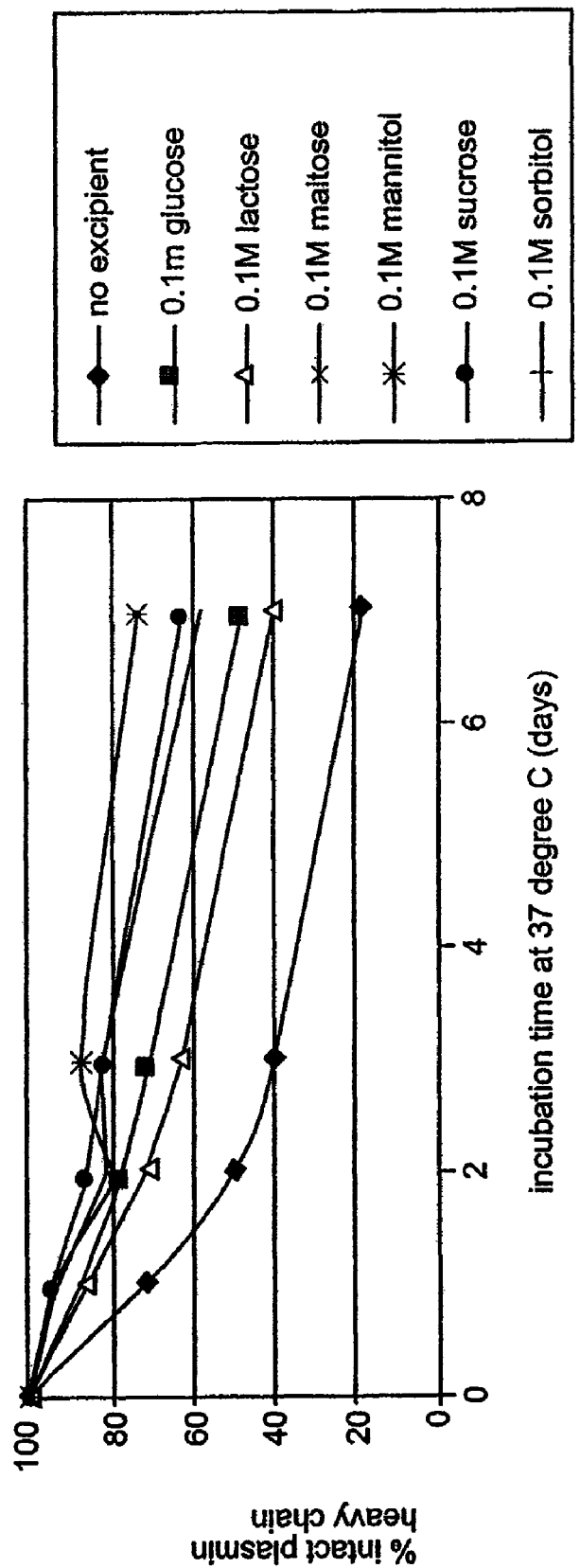
FIG. 5 illustrates the stability at 37° C. of a reversibly inactivated acidified plasmin at pH of 3.7, with carbohydrate stabilizers.

Stabilization of Reversibly Inactivated Acidified Plasmin Composition with a Sugar or Sugar Alcohol Acidified plasmin compositions were formulated according to the present invention, as described n Examples 1 and 2, in 5 mM of acetic acid at pH 3.7 with 0.1M of maltose, mannitol, sucrose or sorbitol added as a stabilizer. A plasmin composition formulated without any excipient was included as a control. All samples were incubated at 37° C. for 7 days and the change in plasmin integrity analyzed using SDS-PAGE under reducing conditions, as described in Example 2 above. FIG. 5 demonstrates that the percent degradation of plasmin in the low pH compositions formulated with a sugar or sugar alcohol are significantly reduced, as compared to the control without a sugar or sugar alcohol.

Example 6

Figure 6:
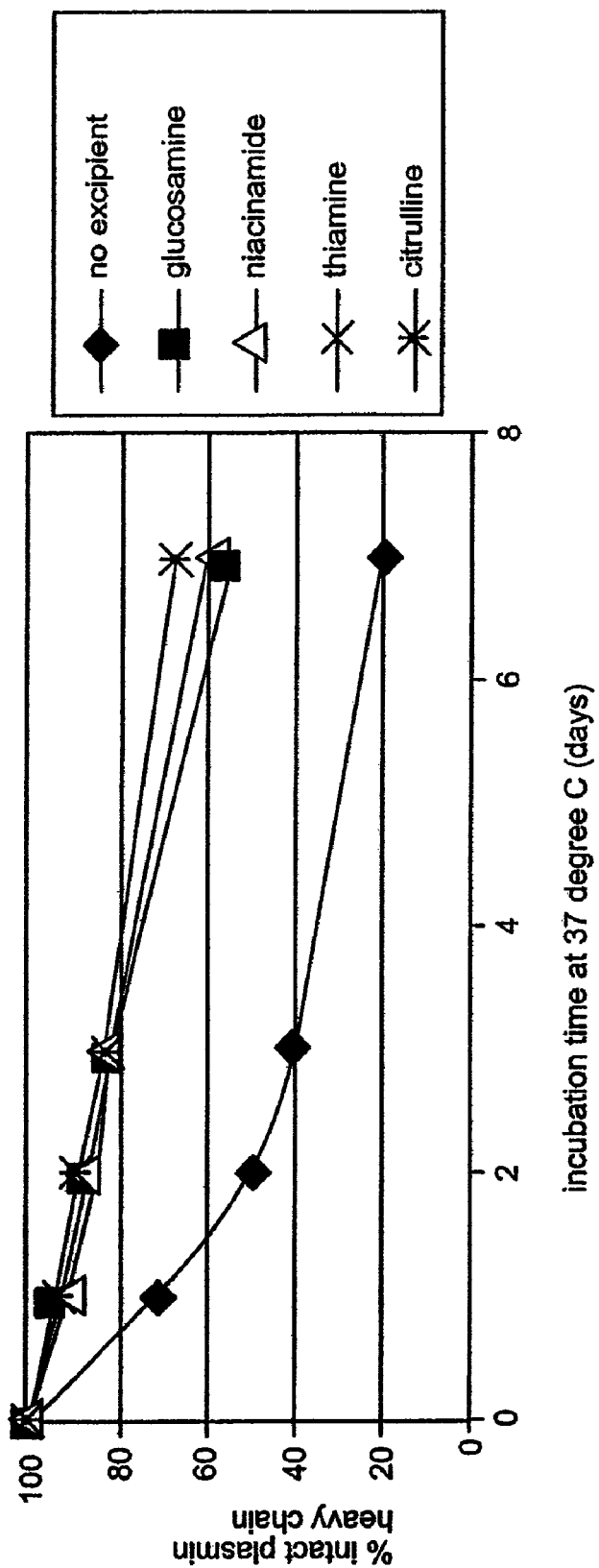
FIG. 6 illustrates the stability at 37° C. of a reversibly inactivated acidified plasmin at a pH of 3.7 with glucosamine, niacinamide, thiamine or citrulline as a stabilizing agent.

Stabilization of Reversibly Inactivated Acidified Plasmin Composition with Non-carbohydrate Stabilizing Agents Reversibly inactivated acidified compositions were formulated at 1 mg/ml in 5 mM acetic acid, pH 3.7, according to the present invention, with 0.1M of glucosamine, niacinamide, citrulline or thiamine added as a non-carbohydrate stabilizer. A reversibly inactivated acidified plasmin formulation without any excipient stabilizing agent was included as a control. All samples were incubated at 37° C. for 7 days and the change in plasmin integrity analyzed using SDS-PAGE under non-reducing conditions. Referring now to FIG. 6, all of the non-sugar stabilizing agents tested improved the stability of the reversibly inactivated acidified plasmin composition at 37° C. over the 7 day test period.

A reversibly inactivated acidified plasmin compositions was also formulated at 1 mg/ml in 2 mM acetic acid, pH 3.4, according to the present invention, with 150 mM sodium chloride as a stabilizing agent. The same formulation, but without sodium chloride, was also prepared and included as a control. Samples were incubated at 4° C. for 28 days. The change in plasmin integrity was analyzed using SDS-PAGE under non-reducing conditions, as described in Example 3 above. The activity was assessed also as described in Example 3. Values were normalized relative to day 0 controls that were assigned a value of 100%. The results, as shown in Table 5, demonstrated that plasmin stored at 4° C. was more stable in the low-pH formulation containing sodium chloride.

TABLE 5

Stability of reversibly inactivated acidified plasmin composition (2 mM sodium acetate, pH 3.4) with or without 150 mM sodium chloride, stored at 4° C.

| Sodium chloride Concentration (mM) | Plasmin (mg/ml) | % intact heavy chain after 28 days | % intact light chain after 28 days | % activity after 28 days |
| --- | --- | --- | --- | --- |
| 0 | 1 | 90 | 93 | 81 |
| 150 | 1 | 101 | 95 | 97 |

(The intact heavy chain, light and potentcy in each formulation were normalized before incubation as 100%)

Example 7

Figure 7:
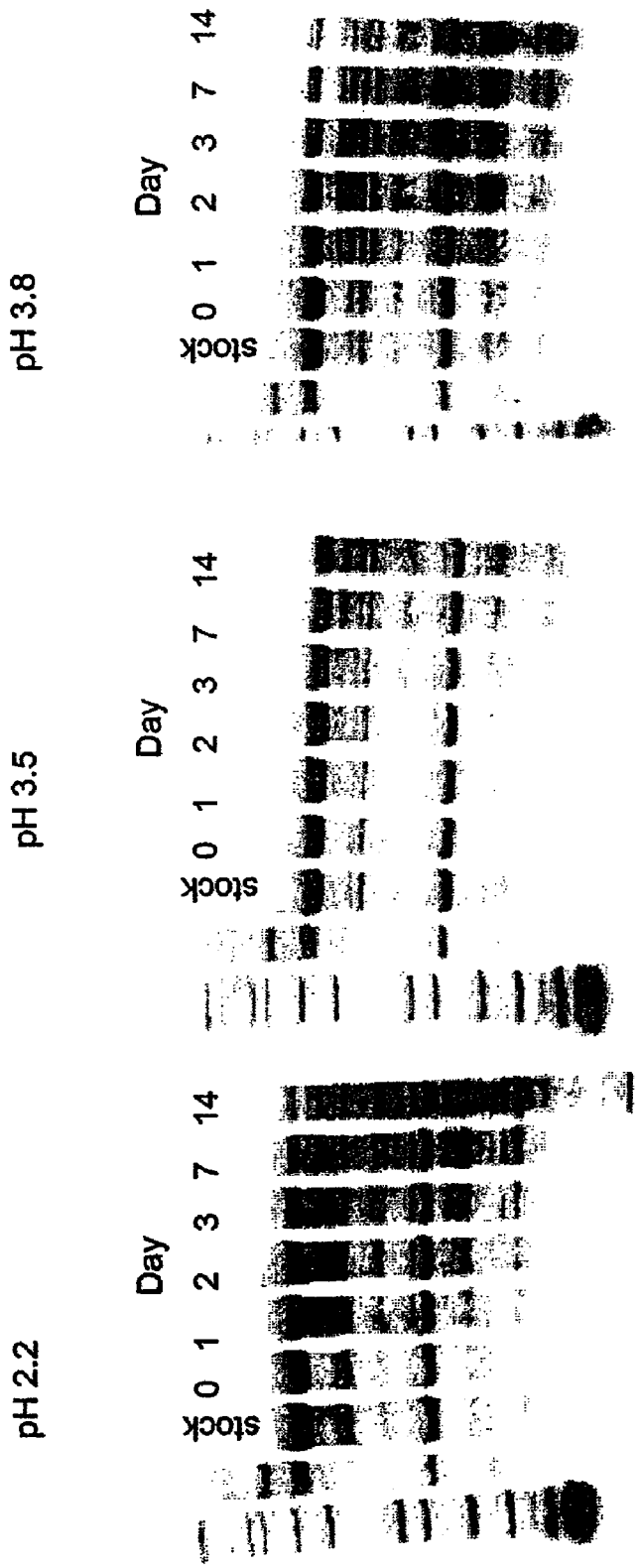
FIG. 7 illustrates the progressive degradation of a plasmin composition at a pH of 2.2, 3.5, or 3.7.

Degradation Pattern of Reversibly Inactivated Acidified Plasmin Composition Characterized by N-terminal Sequencing The degradation peptides of plasmin samples were characterized by N-terminal sequencing as follows. Plasmin compositions were formulated at low pH values: a pH less than 2.5 and a pH of 3.5 and 3.8 containing 2 mM acetic acid. The plasmin samples were analyzed using SDS-PAGE with 4-12% Bis-Tris NuPage gels, as shown in FIG. 7. The protein bands were transferred to a PVDF membrane, stained with Coomassie Blue R-250 (Bio-RAD Laboratories, Hercules, Calif.) and bands cut out using a scalpel.

N-terminal sequence analysis was performed directly from the membrane using a Hewlett Packard 241 Protein Sequencer (Hewlett Packard, Inc., Glen Allen, Va.). Ten cycles were run for each band so that the corresponding fragment of plasmin could be identified. Molecular weights for each band were determined with densitometry analysis using the Mark 12 marker available from Invitrogen, Inc. (San Diego, Calif.)

Figure 8:
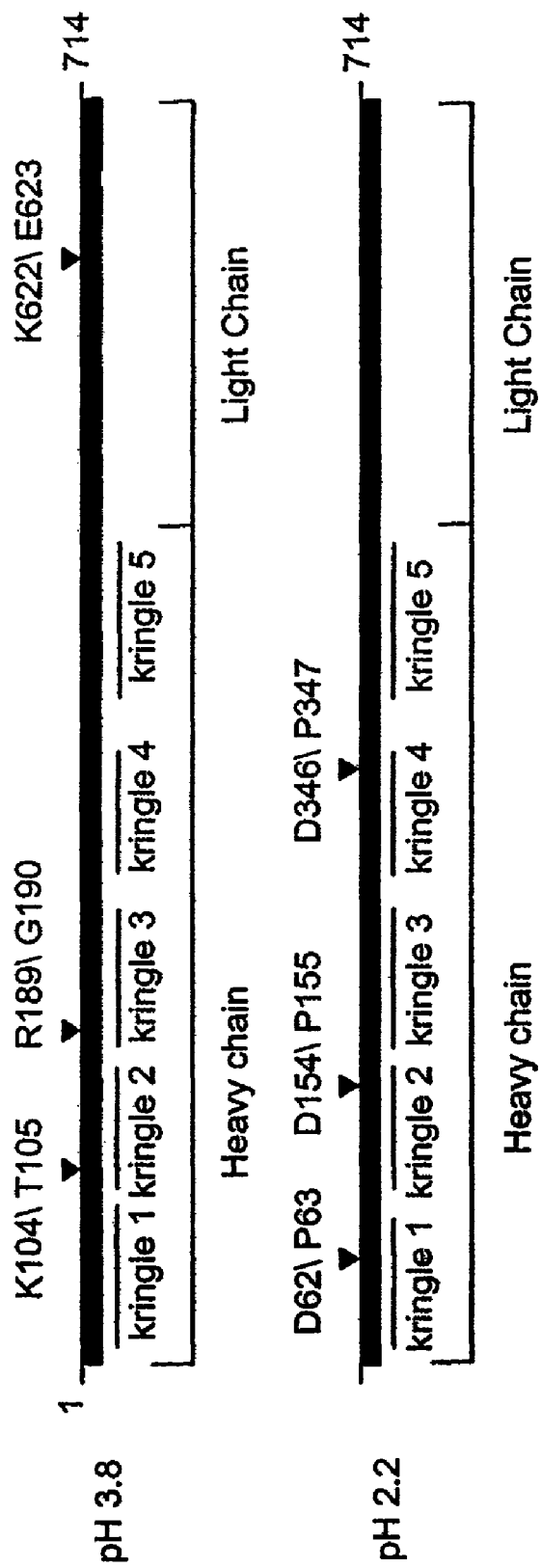
FIG. 8 illustrates the cleavage sites generated in plasmin at pH 2.2 and 3.8.

Three polypeptides generated by incubation of plasmin at pH 3.8 began at positions (numbering relative to Lys-plasmin) threonine (T105), glycine (G190) and glutamic acid (E623). From the known amino acid sequence of plasmin, it was determined that the first two polypeptides were from the heavy chain and the third from the light chain. As shown in FIG. 8, the amino acid preceding the N-terminal amino acid was either arginine or lysine (K104, R189, and K622). It is commonly known that plasmin cleaves proteins on the carboxyl side of lysine and arginine. These results demonstrated that compositions of plasmin at pH 3.8 were susceptible to autodegradation.

Three polypeptides generated by incubation of plasmin at pH 2.2 began with proline at the N-termini. From the known amino acid sequence of plasmin, it was determined that these polypeptides were from the heavy chain, starting at positions P63, P155, and P347, as shown in FIG. 8. The amino acid preceding each proline was an aspartic acid (D62, D154, and D346). It is commonly known that aspartyl-prolyl (D-P) peptide bonds are acid labile. These results demonstrated that compositions of plasmin at pH 2.2 were susceptible to acid hydrolysis of peptide bonds.

Example 8

Low Buffer Capacity of Compositions

Figure 9:
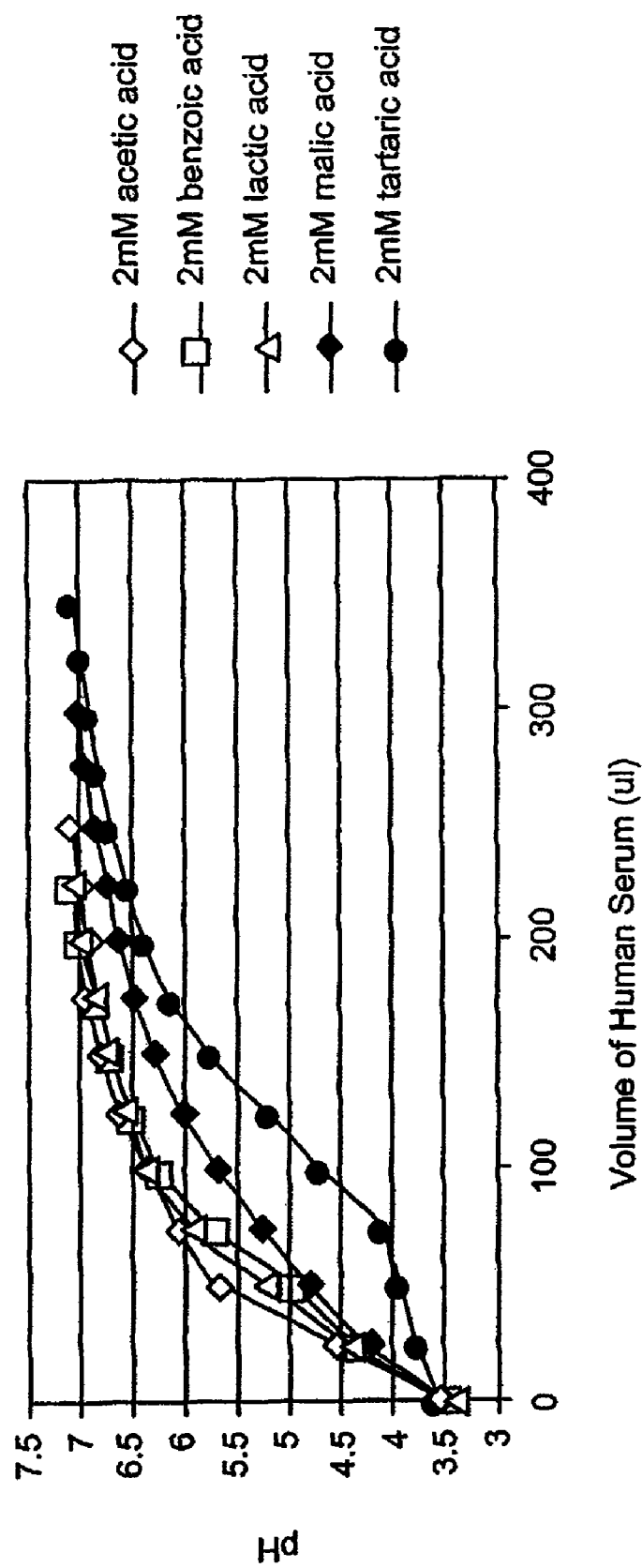
FIG. 9 illustrates the titration, with human serum, of plasmin solutions having various low buffering capacity buffers.

Plasmin (1 mg/ml) was formulated in 2 mM acetic, benzoic, lactic, malic or tartaric acid at pH 3.5. The effect of admixing increasing volumes of human blood serum to the pH of 1 ml of the plasmin solution was measured (FIG. 9). In all cases, only a small amount of serum, typically 10 to 30% of the plasmin volume, was required to achieve a pH of about 7. In a separate experiment, plasmin compositions contained either 5 or 10 mM acetic acid. The volumes of serum required to neutralize the plasmin solution were 30% and 70% of the initial volume. These results demonstrated that low buffering capacity compositions, of typically around 2 mM, but upwards of 100 mM, are readily restored to a pH of about 7. These results also suggest that plasmin would be readily neutralized locally within a thrombus and that large volumes (relative to the liquid fraction of the clot) of plasmin could be used to affect lysis.

Example 9

Lysis of Thrombi by Reversibly Inactivated Acidified Plasmin in an in vitro Thrombus Model To compare the efficacy of plasmin and tPA toward the lysis of long retracted clots, we have developed an in vitro model which would mimic parameters of the clots formed in patients with PAO.

In Vitro PAO Model. Fresh whole human blood was collected into 30×0.95 cm glass tubes and allowed to clot spontaneously without additives. Tubes were incubated for 20 hours at 37° C. to allow full retraction. Retracted clots were separated from serum using USA Standard testing sieves D16 with 14 mesh and their weights were determined. Blood clots were transferred into smaller diameter glass tubes that resembled the average size clots in leg arteries (0.6×12 cm). A multi-side port pulse-spray catheter (French size 5 with the 11 cm spraying tip, Cook, Inc.) was inserted into the clot and a thrombolytic reversibly inactivated acidified plasmin composition according to the present invention, or tPA) at 1 mg/ml was delivered in 1 ml increments separated by 1 hour time intervals. The number of injections corresponds to the dose of thrombolytic. The extent of clot lysis was measured by the weight of a residual clot and expressed as a percent of clot weight reduction. Although this model is called a PAO model, and mimics the dimensions of the clots found in PAO patients, venous blood was used for clot formation. Both tPA and the reversibly inactivated acidified plasmin composition according to the present invention were tested in this model and the results are presented below.

Plasmin is as effective as tPA for lysis of fresh clots, unlike when tPA and plasmin are used for lysis of retracted clots aged for 20 hours to allow complete cross-linking by Factor XIII. tPA is unable to lyse such clots. Clot weight reduction obtained with tPA-treated clots is similar to the control, even when the dose is raised to 5 mg per clot.

Plasmin, on the other hand, is effective toward both fully retracted and cross-linked clots. There is a dose-dependence of the lytic effect of plasmin and after five injections (or 5 mg plasmin in total) the clots are almost completely lysed. In a similar human series of experiments, the same inability to dissolve retracted and cross-linked clots was observed with urokinase. Locally delivered plasmin therefore is a more effective thrombolytic agent than tPA and other plasminogen activators.

These in vitro data show that tPA requires the presence of its substrate, plasminogen, in the clot to initiate and maintain clot lysis. Therefore, while plasmin is as effective as tPA for lysing fresh or plasminogen-rich clots, plasmin is more effective that tPA, and other plasminogen activators, for lysing of long retracted plasminogen-poor clots. Moreover, the data presented in this example demonstrates that plasmin is effective in its reversibly inactivated acidified form when it is injected directly inside the clot.

Figure 10:
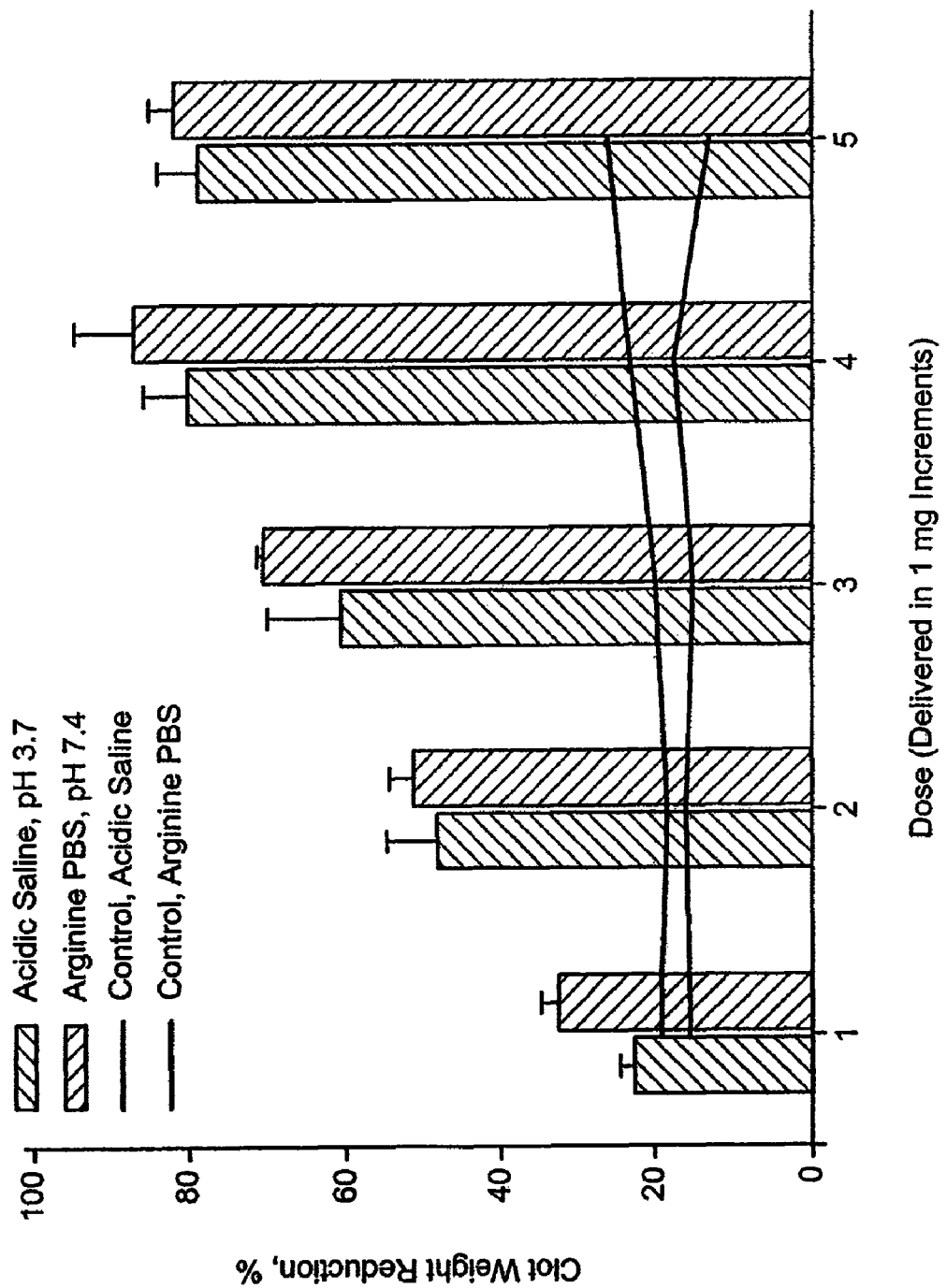
FIG. 10 compares the thrombolytic potency of plasmin in saline at pH 3.7 with plasmin neutralized before injection into the clot.

The PAO model as described above was used to compare the efficacy of plasmin (1 mg/ml) formulated in a low pH formulation described in this invention (saline, pH 3.7) with a neutral pH plus stabilizer formulation. The results are demonstrated in FIG. 10 and show that the low pH formulation is as efficacious as the neutral pH plus stabilizer formulation.

Example 10

Trypsin Stabilized at Low pH can be Reactivated by Transfer to Higher pH Environment Trypsin (16.4 mg, Sigma Chemical Co. Catalog No. T-1426) was dissolved in 2.28 ml of 50 mM Tris/0.5M NaCl (pH 8.0). The trypsin solution was loaded onto a 1-ml column of Benzamidine-Sepharose (Pharmacia Code No. 17-0568-01) that had been pre-equilibrated with 50 mM Tris/0.5M NaCl (pH 8.0). This column was washed with 4 ml of this latter buffer, resulting in a decrease in the eluate absorbance (280 nm) to less than 0.03. Trypsin was eluted from this column in an inactivated state with 0.5-ml volumes of 200 mM glycine/0.5M NaCl (pH 3.0); the third through fifth 0.5-ml fractions eluted from this column contained the peak values of absorbance (280 nm) and were pooled. The absorbance (280 nm) of this pooled trypsin eluate was determined to be 9.22; based upon the extinction coefficient for trypsin ($E_{280}$ for a 1% solution=17.09) and the molecular weight of trypsin (24,000), the concentration of total trypsin protein in this pooled column eluate was calculated to be 225 µM.

The concentration of trypsin active sites in this pooled trypsin column eluate was determined by the method described by Case & Shaw, Biochem. Biophys. Res. Commun. 29, 508 (1967) and incorporated herein by reference in its entirety, using p-nitrophenylguanidinobenzoate as active-site titrant. This assay was performed at pH 8.3, by diluting a small volume (100 µl) of the pooled trypsin column eluate into an assay mixture also containing 700 µl of 50 mM sodium borate (pH 8.3), 200 µl of 10 mM sodium phosphate/% glycine (pH 7.0) plus 10 µl of p-nitrophenylguanidininobenzoate (dissolved in dimethyl formamide); the final pH of this mixture composition was determined to be 8.3. The trypsin-dependent amount of p-nitrophenol formed in this assay was monitored at 410 nm. Based upon the extinction coefficient for p-nitrophenol at 410 nm and at pH 8.3 ($16,595\ M^{-1}$), 100 µl of this pooled trypsin column eluate present in the 1.01-ml assay corresponded to a concentration of 22.95 µM trypsin active sites present in the cuvette. Therefore, the original stock solution of pooled trypsin column eluate contained 231 µM trypsin active sites. This latter value is identical, within experimental error, to the concentration of total trypsin protein present (225 µM). These results demonstrate that trypsin can be adjusted to low pH and then transferred to a higher pH environment with reactivation of its active site.

What is claimed is:

1. A method of treating a subject suffering from a disorder susceptible to improvement with plasmin comprising administering to the subject a therapeutically effective amount of a composition comprising:
   a reversibly inactivated, acidified plasmin, the plasmin being substantially free of a plasminogen activator; and
   a low buffering capacity buffer;
   wherein the composition is a solution suitable for pharmaceutical use that can be raised to physiological pH by adding no more than about 5 volumes of serum to the solution relative to a volume of the solution.

2. The method of claim 1, wherein the plasmin is Glu-plasmin, Lys-plasmin, midi-plasmin, mini-plasmin, or micro-plasmin.

3. The method of claim 1, wherein the composition further comprises an aqueous carrier.

4. The method of claim 1, wherein the composition further comprises an anticoagulant.

5. The method of claim 1, wherein the composition has a pH of about 2.5 to about 4.

6. The method of claim 1, wherein the composition is a sterile solution suitable for parenteral administration to humans.

7. The method of claim 1, wherein the buffer comprises at least one acid.

8. The method of claim 7, wherein the acid is in the concentration range of about 1 mM to about 100 mM.

9. The method of claim 1, wherein the buffer comprises a carboxylic acid, at least one amino acid, a dipeptide, an oligopeptide which includes the at least one amino acid, or a combination thereof.

10. The method of claim 1, wherein the buffer is formic acid, acetic acid, citric acid, hydrochloric acid, lactic acid, malic acid, tartaric acid, benzoic acid, serine, threonine, methionine, glutamine, alanine, glycine, isoleucine, valine, aspartic acid, or combinations thereof.

11. The method of claim 1, wherein the plasmin is in the concentration range of about 0.01 mg/ml to about 50 mg/ml.

12. The method of claim 1, wherein the composition further comprises a stabilizing agent.

13. The method of claim 12, wherein the stabilizing agent is a polyhydric alcohol, a salt, citrulline, or combinations thereof.

14. The method of claim 12, wherein the stabilizing agent is a pharmaceutically acceptable carbohydrate, salt, glucosamine, thiamine, niacinamide, citrulline, or combinations thereof.

15. The method of claim 12, wherein the stabilizing agent is a sugar or sugar alcohol selected from the group consisting of glucose, maltose, mannitol, sorbitol, sucrose, lactose, trehalose, and combinations thereof.

16. The method of claim 12, wherein the stabilizing agent is selected from the group consisting of monosacchrides, disaccharides, polysaccharides, polyhydric alcohols, and combinations thereof.

17. The method of claim 12, wherein the stablizing agent is a carbohydrate having a concentration in the range of about 0.2% w/v to about 20% w/v.

18. The method of claim 12, wherein the stabilizing agent is selected from the group consisting of sodium chloride, potassium chloride, magnesium chloride, calcium chloride, manganese chloride, and combinations thereof.

19. The method of claim 12, wherein the stabilizing agent is selected from the group consisting of a salt, glucosamine, thiamine, niacinamide, and combinations thereof, and the concentration of the stabilizing agent is in the range of about 0.01M to about 1M.

20. The method of claim 1, wherein the composition can be raised to physiological pH by adding no more than about one volume of serum to the solution relative to a volume of the solution.

* * * * *